United States Patent
Chen

(10) Patent No.: US 12,023,661 B2
(45) Date of Patent: Jul. 2, 2024

(54) NITROGEN HETEROCYCLIC CARBENE LIGANDS AND RUTHENIUM CATALYSTS THEREOF, PREPARATION METHOD THEREFOR AND APPLICATION THEREOF

(71) Applicant: PAIMAI NEW MATERIALS (CHENGDU) CO., LTD., Sichuan (CN)

(72) Inventor: Jianxin Chen, Sichuan (CN)

(73) Assignee: PAIMAI NEW MATERIALS (CHENGDU) CO., LTD., Sichuan (CN)

(*) Notice: Subject to any disclaimer, the term of this patent is extended or adjusted under 35 U.S.C. 154(b) by 544 days.

(21) Appl. No.: 17/420,409

(22) PCT Filed: Aug. 19, 2019

(86) PCT No.: PCT/CN2019/101411
§ 371 (c)(1),
(2) Date: Jul. 2, 2021

(87) PCT Pub. No.: WO2020/140441
PCT Pub. Date: Jul. 9, 2020

(65) Prior Publication Data
US 2022/0161246 A1    May 26, 2022

(30) Foreign Application Priority Data
Jan. 2, 2019  (CN) .................. 201910002812.2

(51) Int. Cl.
*B01J 31/22* (2006.01)
*C07C 67/333* (2006.01)
(Continued)

(52) U.S. Cl.
CPC ....... *B01J 31/2278* (2013.01); *B01J 31/2273* (2013.01); *C07C 67/333* (2013.01);
(Continued)

(58) Field of Classification Search
None
See application file for complete search history.

(56) References Cited

U.S. PATENT DOCUMENTS 8,299,021 B2   10/2012  Blatt et al.
2012/0149840 A1  6/2012  Mueller et al.

FOREIGN PATENT DOCUMENTS

| CN | 110041262 A | 7/2019 |
| WO | 2007075427 A1 | 7/2007 |
| WO | 2011091757 A1 | 8/2011 |

OTHER PUBLICATIONS

Shawna, L.B. et al.; Olefin Metathesis Catalysts Bearing a pH-responsive NHC Ligand: a Feasible Approach to Catalyst Separation from RCM Products; Dalton Transactions, vol. 42, Sep. 12, 2008, pp. 5791-5799, especially, p. 5791, abstract, p. 5792, schemes 1-2.

(Continued)

*Primary Examiner* — Catherine S Branch
(74) *Attorney, Agent, or Firm* — NKL Law; Allen Xue

(57) ABSTRACT

Nitrogen heterocyclic carbine ligands and ruthenium catalysts thereof, a preparation method therefor and an application thereof are provided. The structures of the nitrogen heterocyclic carbine ligands are represented by formulas Ia and Ib, respectively, and the corresponding ruthenium catalyst structures are represented by IIa and IIb, respectively. After simultaneously introducing large-steric hindrance and electron-rich groups into the described nitrogen heterocyclic carbine ligand structures, the catalytic activity, stability and application range of the ruthenium complex catalysts thereof are significantly improved.

(Continued)

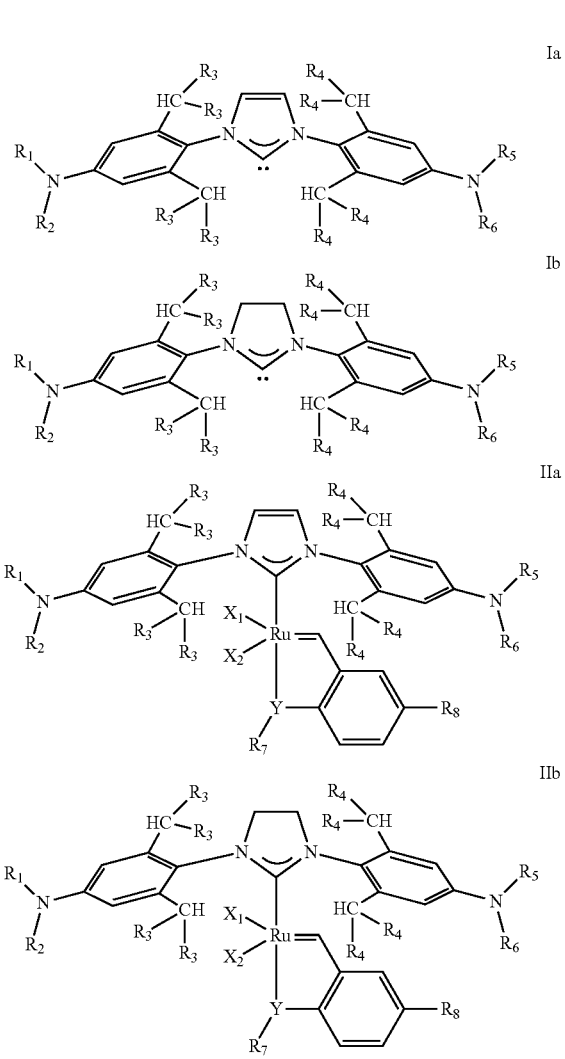

14 Claims, 1 Drawing Sheet

(51) Int. Cl.
C07D 233/16 (2006.01)
C07D 487/04 (2006.01)
C07F 15/00 (2006.01)
C08G 61/08 (2006.01)

(52) U.S. Cl.
CPC ......... *C07D 233/16* (2013.01); *C07D 487/04* (2013.01); *C07F 15/0046* (2013.01); *C08G 61/08* (2013.01); *B01J 2231/54* (2013.01); *B01J 2231/60* (2013.01); *B01J 2531/821* (2013.01); *C08G 2261/11* (2013.01); *C08G 2261/3325* (2013.01); *C08G 2261/418* (2013.01)

(56) References Cited

OTHER PUBLICATIONS

Gomez-Suarez, A. et al.; [{Au(NHC)}2(μ-OH)][BF4]: Silver-Free and Acid-Free Catalysts for Water-Inclusive Gold-Mediated Organic Transformations; Organometallics, vol. 32, No. (4), Feb. 6, 2013, pp. 1106-1111, especially, p. 1107, picture 1.

Dröge, Thomas et al.; The Measure of All Rings—N-Heterocyclic Carbenes; Angewandte Chemie International Edition. 2010, 49, pp. 6940-6952.

Fortman, George C. et al.; N-Heterocyclic carbene (NHC) ligands and palladium in homogeneous cross-coupling catalysis: a perfect union; Chem. Soc. Rev., 2011, 40, Jul. 6, 2011, pp. 5151-5169.

Thiel, Vasco et al.; On the Mechanism of the Initiation Reaction in Grubbs-Hoveyda Complexes;J. American Chemical Society, 2012,134(2), Dec. 21, 2011, pp. 1104-1114.

Berthon-Gelloz, Guillaume et al.; IPr an easily accessible highly hindered N-heterocyclic carbene; Dalton Transactions, 2010, 39, Nov. 27, 2009, pp. 1444-1446.

Arduengo, Anthone J. et al.; Imidazolylidenes, Imidazolylidenes and Imidazolidines; Tetrahedron, 55 (1999),14523-14534.

Hoveyda, Amir H. et al.; Efficient and Recyclable Monomeric and Dendritic Ru-Based Metathesis Catalysts; J. American Chemical Society. 2000, vol. 122, No. 34, Aug. 12, 2000, pp. 8168-8179.

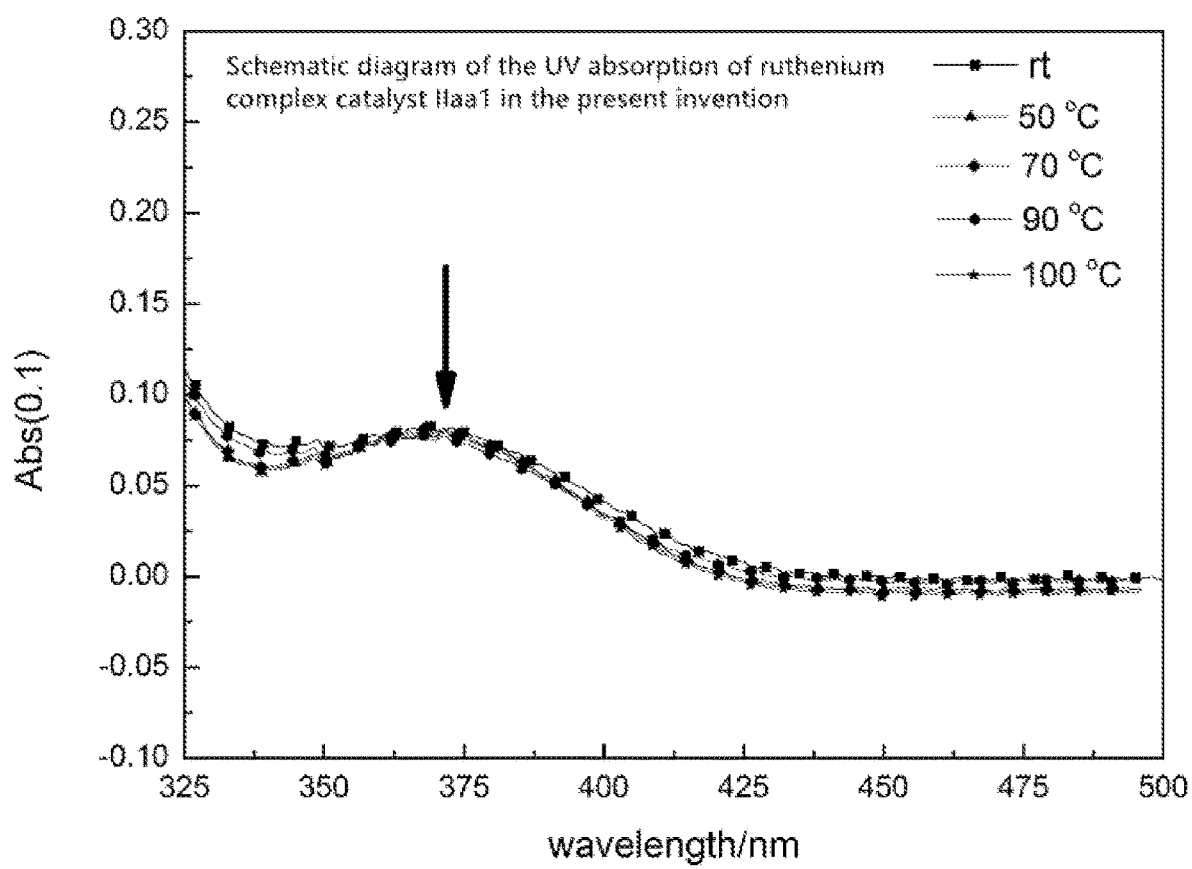

NITROGEN HETEROCYCLIC CARBENE LIGANDS AND RUTHENIUM CATALYSTS THEREOF, PREPARATION METHOD THEREFOR AND APPLICATION THEREOF

TECHNICAL FIELD

The present invention relates to the structure of a N-heterocyclic carbene (NHC) ligand, the ruthenium complex catalyst thereof, and the use thereof.

BACKGROUND TECHNOLOGY

The research and development of ruthenium complex catalysts (especially Grubbs catalysts) and their catalysis in metathesis and hydrogenation of olefins have attracted extensive attention in this field. In particular, the intramolecular ring-closing metathesis has been widely used in the field of organic drugs worldwide, while the olefin metathesis polymerization has important applications in new materials and other fields.

The second-generation Grubbs catalyst has higher activity and selectivity as well as better stability than the first-generation catalyst due to the incorporation of a N-heterocyclic carbene (NHC) ligand on the ruthenium metal, which has a stronger electron-donating ability and better stability than the phosphine ligand. Hoveyda research group introduced a bulky nucleophilic complex ligand into Grubbs catalyst to form H-G catalyst, which can improve the thermal stability of the catalyst. Zhan research group further improved the activity of ruthenium complex by changing the substituents of Hoveyda complex ligand and introducing electron-withdrawing substituents such as aminosulfonyl, nitro and carbonyl to obtain a series of catalysts.

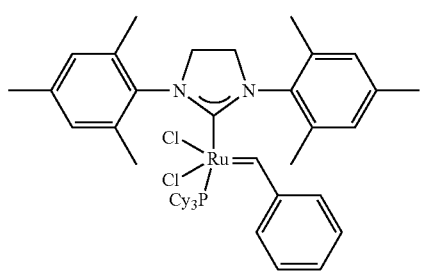

Grubbs II

H-G II

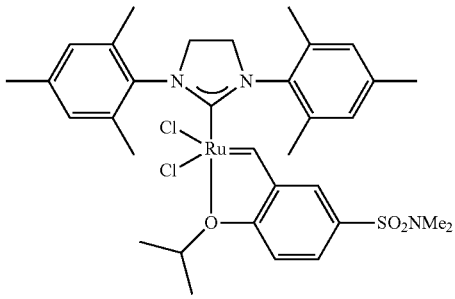

Zhan 1B

The current study on N-heterocyclic carbene (NHC) ligand shows that its structure and electronic effects have a direct impact on the performance of the catalyst. In general, increasing the steric effect of substituents in the nitrogen of imidazole ring (*Angew Chem. Int. Ed* 2010, 49, 6940-6952) and improving the electron-donating ability of N-heterocyclic carbine (*Chem. Soc. Rev.* 2011, 40, 5151-5169) are beneficial to enhancing the activity and stability of the catalyst.

Hans-Jorg Schanz team modified the structure of H-G catalyst based on the above conclusion, and substituting the methyl at the 4-position of aromatic ring substituent in the nitrogen atom of imidazole ring of N-heterocyclic carbene in H-G catalyst with a more electron-donating dimethylamino to obtain the catalyst ITap, which was subjected to the olefin metathesis reaction, and the activity was compared with that of H-G catalyst. The activity of ITap catalyst was higher when catalyzing ROMP (i.e. ring-opening metathesis polymerization) of cyclooctene (COE); while the activity of H-G catalyst was higher, when catalyzing RCM (intramolecular ring-closing metathesis) of dimethyl diallylmalonate (DEDAM), that is, for different types of olefin metathesis reactions, both catalysts show different activities (*Dalton Trans.*, 2008, 5791-5799). However, these catalysts still have some problems, such as unsatisfactory catalytic activity and stability, as well as easy decomposition at higher temperatures.

CONTENT OF THE INVENTION

In view of this, the present invention provides a new structure of N-heterocyclic carbene (NHC) ligand, the ruthenium complex catalyst thereof, and the use thereof, in order to solve the deficiencies of the above-mentioned catalysts.

N-heterocyclic carbene ligands of the present invention have the structures of formula Ia and Ib, respectively:

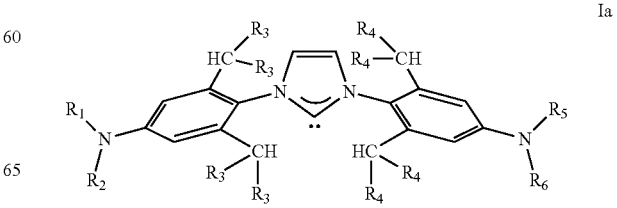

Ia

-continued

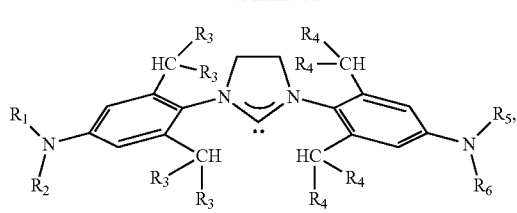
Ib in which each of $R_1$, $R_2$, $R_5$ and $R_6$ is independently selected from the group consisting of $C_1$-$C_{20}$ alkyl or cycloalkyl, $C_1$-$C_{20}$ alkoxy and $C_6$-$C_{20}$ aryl; or $R_1$ and $R_2$ and/or $R_5$ and $R_6$, together with N to which they are linked, each form a heterocyclic group;

Each of $R_3$ and $R_4$ is independently selected from the group consisting of substituted or unsubstituted $C_6$-$C_{20}$ aryl, substituted or unsubstituted $C_6$-$C_{20}$ aryloxy, substituted or unsubstituted $C_2$-$C_{20}$ heterocyclic aryl, wherein at least one of the substituents is selected from the group consisting of $C_1$-$C_{10}$ alkyl, $C_1$-$C_{10}$ alkoxy, hydroxyl, thiohydroxyl, ether group, thioether group, keto, aldehyde group, ester group, amino, imino, amido, nitro, carboxyl, disulfide group, carbonate group, isocyanate group, carbodiimide group, alkoxycarbonyl, carbamate group or halogens.

As a preferable structure of the formula Ia and/or Ib mentioned above, $R_3$ and $R_4$ are each independently selected from the group consisting of $C_6$-$C_{20}$ aryl, $C_6$-$C_{20}$ aryloxy and $C_2$-$C_{20}$ heterocyclic aryl.

As a further preferable structure of the formula Ia and/or Ib mentioned above, $R_3$ and $R_4$ are each independently selected from $C_6$-$C_{20}$ aryl.

Further, for N-heterocyclic carbene ligands of the present invention with the structure of formula Ia, the structures of formula Iaa, formula Iab, formula Iac or formula Iad are preferable; and the structure of formula Iaa is more preferable:

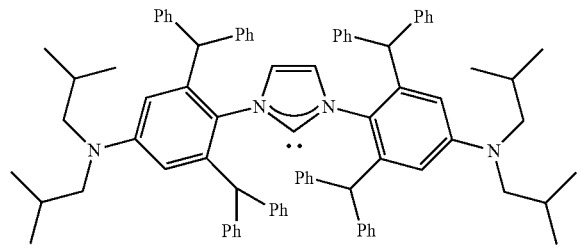
Iaa

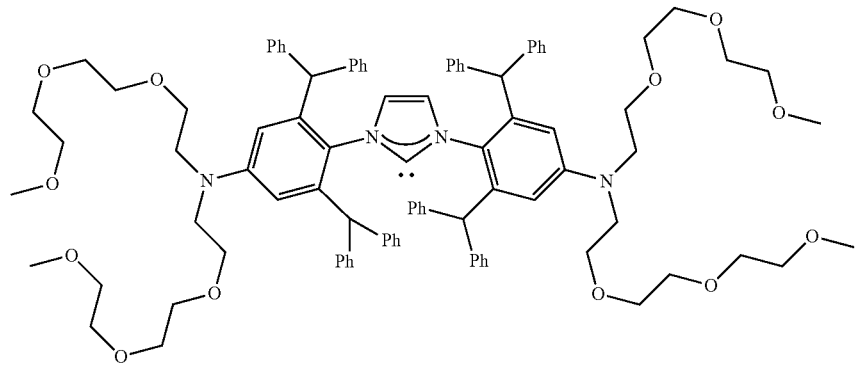
Iab

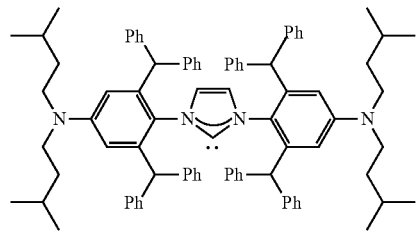
Iac

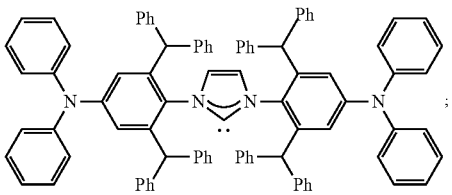
Iad

N-heterocyclic carbene ligands with the structure of formula Ib preferably have the structure of formula Iba:

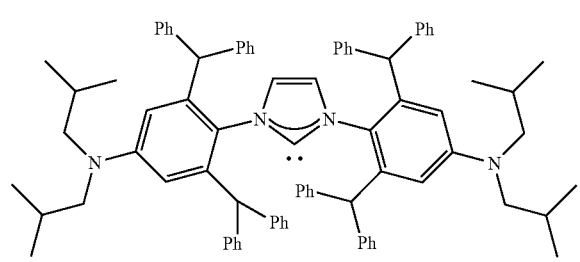

Iba

The ruthenium complex catalyst with N-heterocyclic carbene ligand mentioned above has the structures of formulae Ia and Ib, respectively:

IIa

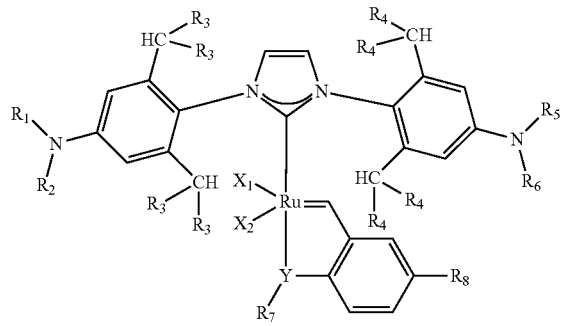

IIb in which each of $R_1$, $R_2$, $R_5$ and $R_6$ is independently selected from the group consisting of $C_1$-$C_{20}$ alkyl or cycloalkyl, $C_1$-$C_{20}$ alkoxy and $C_6$-$C_{20}$ aryl; or $R_1$ and $R_2$ and/or $R_5$ and $R_6$, together with N to which they are linked, each form a heterocyclic group;
$R_3$ and $R_4$ are each independently selected from the group consisting of substituted or unsubstituted $C_6$-$C_{20}$ aryl, substituted or unsubstituted $C_6$-$C_{20}$ aryloxy, and substituted or unsubstituted $C_2$-$C_{20}$ heterocyclic aryl, wherein at least one of the substituents is selected from the group consisting of $C_1$-$C_{10}$ alkyl, $C_1$-$C_{10}$ alkoxy, hydroxyl, thiohydroxyl, ether group, thioether group, keto, aldehyde group, ester group, amino, imino, amido, nitro, carboxyl, disulfide group, carbonate group, isocyanate group, carbodiimide group, alkoxycarbonyl, carbamate group or halogens;
$R_7$ is selected from the group consisting of H, $C_1$-$C_{15}$ alkyl, $C_1$-$C_{15}$ alkoxy, $C_1$-$C_{15}$ thioether group, $C_1$-$C_{15}$ silyl, $C_1$-$C_{15}$ siloxy, $C_6$-$C_{15}$ aryl, $C_6$-$C_{15}$ aryloxy, $C_6$-$C_{15}$ heterocyclic aryl, $C_2$-$C_{15}$ heterocyclyl, sulfinyl, sulfonyl, $C_1$-$C_{15}$ carbonyl, $C_1$-$C_{15}$ ester group, $C_1$-$C_{15}$ amido, $C_1$-$C_{15}$ ureido, and $C_1$-$C_{15}$ sulfonamido;
$R_8$ is selected from the group consisting of H, F, Cl, Br, nitro, nitrile, formyl, $C_1$-$C_{15}$ aminosulfonyl, $C_1$-$C_{15}$ aminocarbonyl, $C_1$-$C_{15}$ carbonyl, $C_1$-$C_{15}$ ester group, $C_1$-$C_{15}$ amido-, $C_1$-$C_{15}$ ureido or $C_1$-$C_{15}$ sulfonamido;
$X_1$ and $X_2$ are Cl or RCOO—, in which R is $C_1$-$C_{20}$ alkyl;
Y is O, S, N or P.

The preferable structure of the above catalyst may include:
$X_1$ and/or $X_2$ in the formula IIa and/or IIb are chlorine, and Y is oxygen; and/or
$R_7$ in said formula IIa and/or IIb is isopropyl or isobutyl; and/or
$R_8$ in said formula IIa and/or IIb is selected from the group consisting of H, nitro, and $C_1$-$C_{15}$ aminosulfonyl.

For the ruthenium catalyst of the present invention having the structure of formula IIa, the structures of formula IIaa1, formula IIaa2 or formula IIaa3 are preferable:

IIaa1

IIaa2

IIaa3 for said ruthenium catalyst having the structure of formula IIb, the structures of formula IIba1, formula IIba2 or formula IIba3 are preferable:

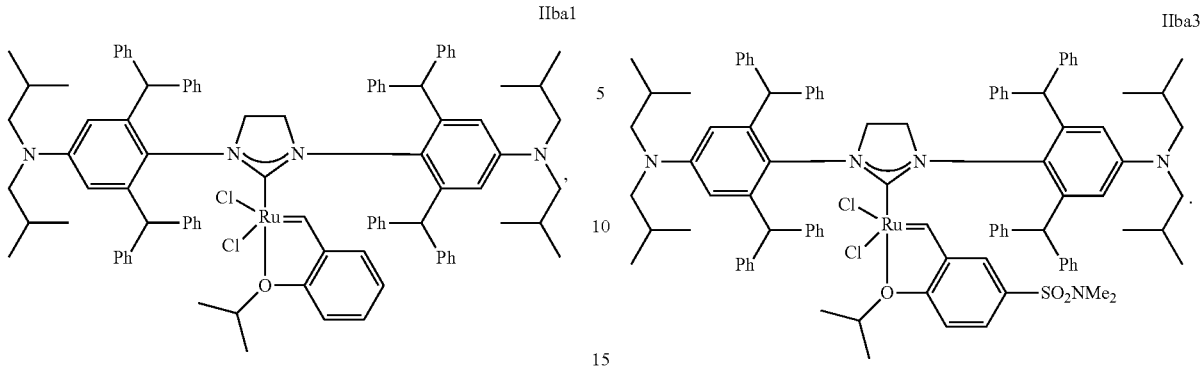

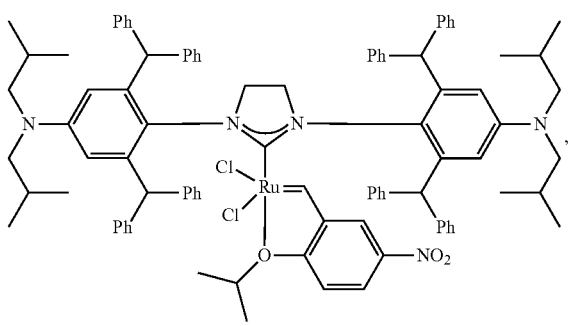

According to the current reports on the related research and/or use of various N-heterocyclic carbene ligand structures and corresponding metal complex catalysts, the above N-heterocyclic carbene ligand structures and corresponding ruthenium complex catalysts of the present invention can be prepared by the methods in the prior art.

For example, the preparation of N-heterocyclic carbene ligand of the present invention can be performed by the corresponding reported methods, such as Guillaume Berthon-Gelloz et al, *Dalton Trans.,* 2010, 39, 1444-1446, etc. After the intermediate of formula (VI) or formula (VII) is synthesized from the corresponding substituted aniline, the N-heterocyclic carbene ligands corresponding to the structures of formula Ia or Ib are prepared from the intermediates of formula (VI) or (VII), respectively. The synthetic routes and procedures are as follows:

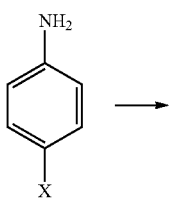

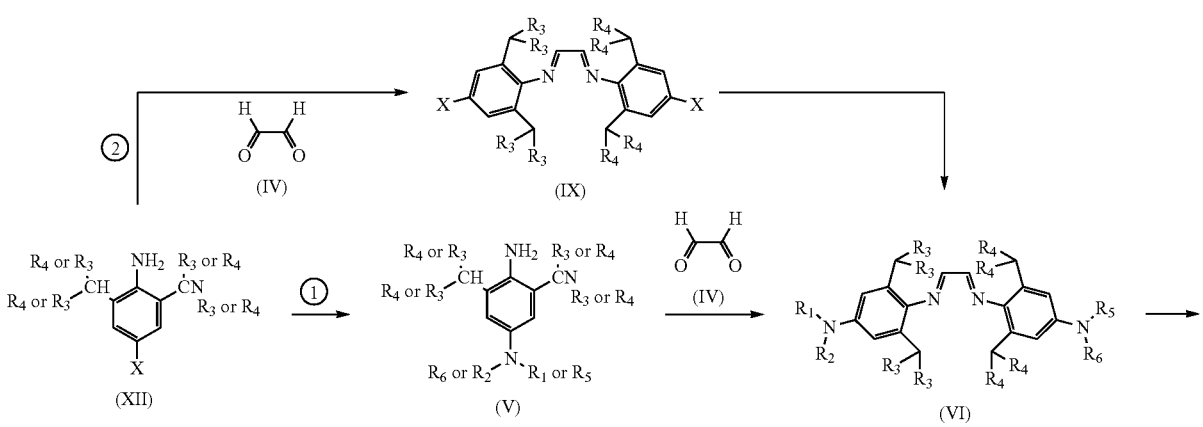

-continued

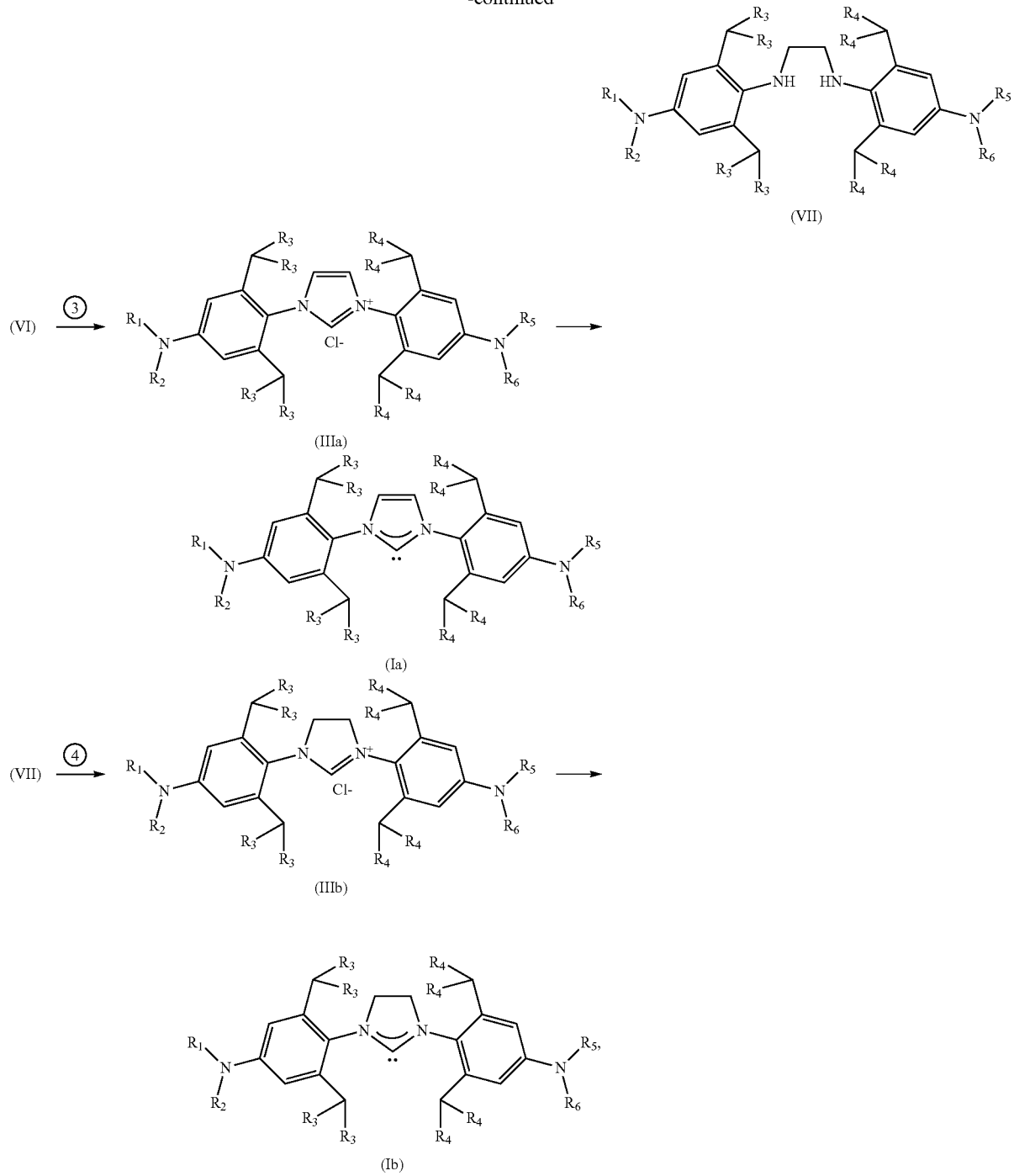

in which each of $R_1$, $R_2$, $R_5$ and $R_6$ is independently selected from the group consisting of $C_1$-$C_{20}$ alkyl or cycloalkyl, $C_1$-$C_{20}$ alkoxy, $C_6$-$C_{20}$ aryl; or $R_1$ and $R_2$ and/or $R_5$ and $R_6$, together with N to which they are linked, each form a heterocyclic group;

$R_3$ and $R_4$ are each independently selected from the group consisting of substituted or unsubstituted $C_6$-$C_{20}$ aryl, substituted or unsubstituted $C_6$-$C_{20}$ aryloxy, substituted or unsubstituted $C_2$-$C_{20}$ heterocyclic aryl, wherein at least one of the substituents is selected from the group consisting of $C_1$-$C_{10}$alkyl, $C_1$-$C_{10}$ alkoxy, hydroxyl, thiohydroxyl, ether group, thioether group, keto, aldehyde group, ester group, amino, imino, amido, nitro, carboxyl, disulfide group, carbonate group, isocyanate group, carbodiimide group, alkoxycarbonyl, carbamate group or halogens;

X is selected from the group consisting of —$NO_2$, I, Br, Cl, $OSO_2Ar$ and $OSO_2CF_3$.

wherein, as the intermediate product (V) of the indirect precursors (VI) and (VII) from which the corresponding N-heterocyclic carbene ligands having the structure of formula Ia or Ib are prepared, at least the following types of structures may be included:

Va

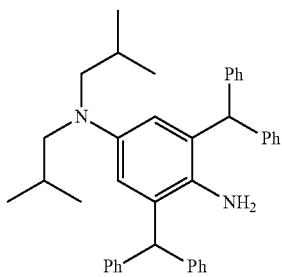

Vb

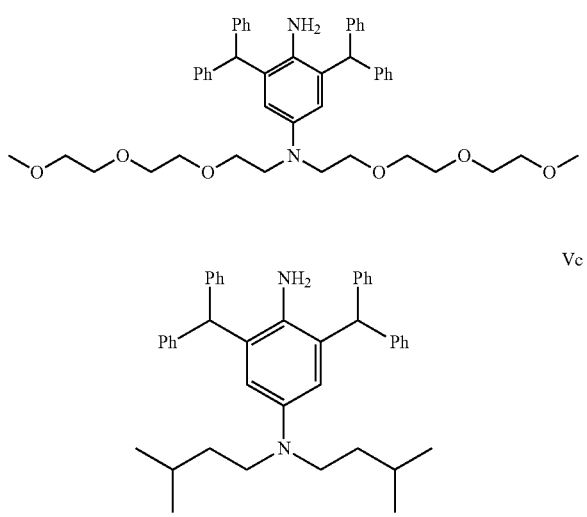

Vc

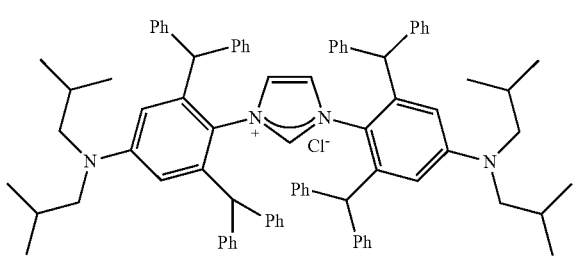

Vd

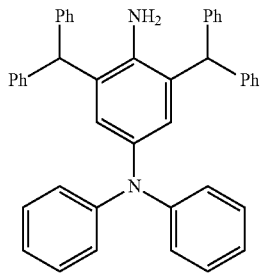

As for the preparation of intermediate product (V) in the first step (1), for example, when X is —NO$_2$, the intermediate product (V) can be prepared from the starting material p-nitroaniline by Friedel-Craft reaction, hydrogenation reaction, and then the reaction with halogenates; when X is the other groups, the para-substituted aniline can be subjected to Friedel-Craft reaction, and then C—N coupling reaction with diamine under the catalysis of palladium catalyst, to prepare the intermediate product (V).

In addition to the preparation of indirect precursor (VI) from intermediate product (V), the compound (VI) can be prepared by the condensation of compound (XII) with glyoxal (or glyoxal derivatives) in step (2) and then by C—N coupling reaction with diamine.

The direct precursor compound (IIIa) was prepared by the reaction of the indirect precursor (VI) with paraformaldehyde in the step (3), in which N-heterocyclic carbene ligand of formula Ia is synthesized from the indirect precursor (VI); then NHC structure of formula Ia can be prepared in situ after the direct precursor (IIIa) is reacted with potassium tert-butoxide under the protection of inert gas, wherein the direct precursor IIIa comprises at least:

IIIaa

IIIab

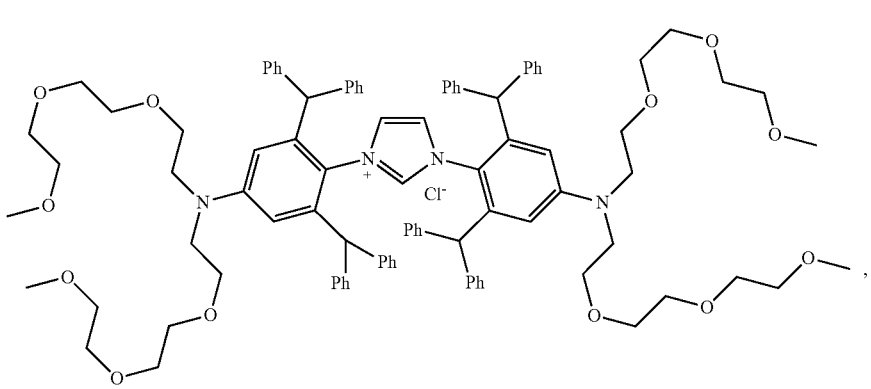

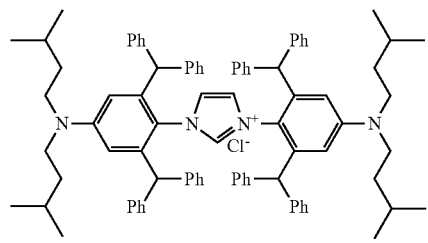

IIIac

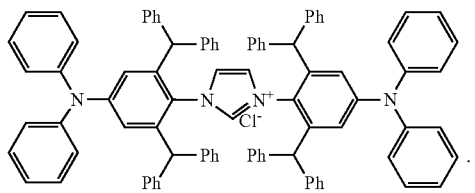

IIIad

When preparing the N-heterocyclic carbene ligand of formula Ib from the indirect precursor (VI), by referring to the methods in the literature including Anthony J. Arduengo, III et al, *Tetrahedron,* 55(1999), 14523-14534, etc, the indirect precursor (VI) can be reduced by sodium borohydride to obtain the indirect precursor (VII), and then react with triethyl orthoformate in step (4), to obtain the corresponding direct precursor (IIIb); then, the NHC structure of formula Ib can be prepared in situ after the direct precursor (IIIb) is reacted with potassium tert-butoxide under the same inert gas. Wherein, the direct precursor compound (IIIb) comprises at least the following compounds, and the structure of formula (IIIba) is preferable:

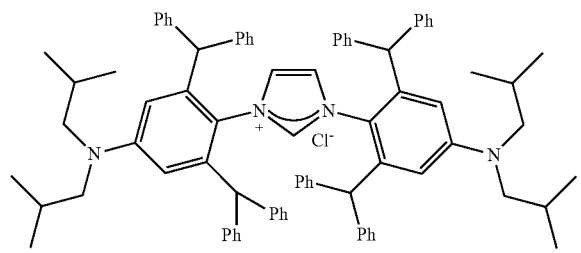

IIIba

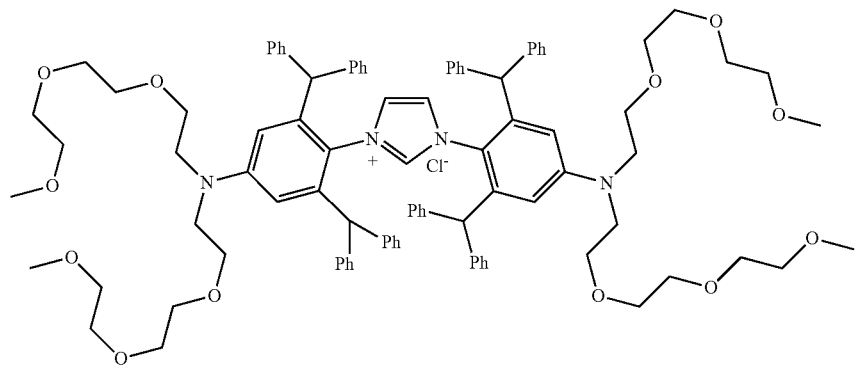

IIIbb

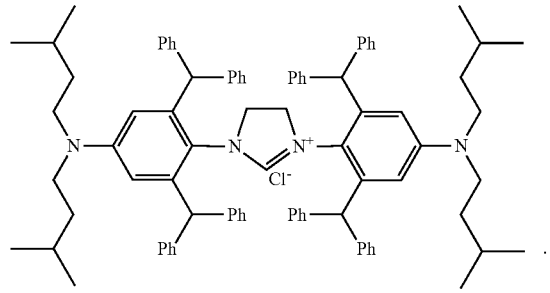

IIIbc

Further preparation of the ruthenium complex catalyst of the present invention from the N-heterocyclic carbene ligand having the structure of formula Ia or Ib prepared above or by other appropriate routes, may also be performed by referring to the reported preparation methods for the study and/or use of metal complex catalysts of various N-heterocyclic carbene ligands such as Amir H. Hoveyda et al, *J. Am. Chem. Soc.* 2000, 122, 8168-8179, et al., which can be carried out in one of the following schemes:

Scheme 1

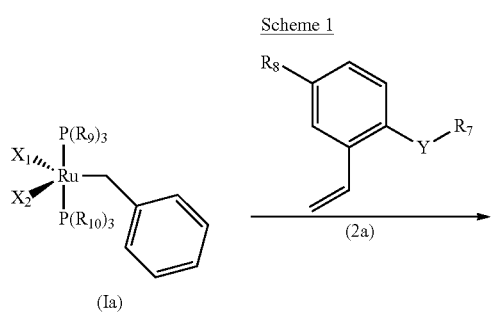

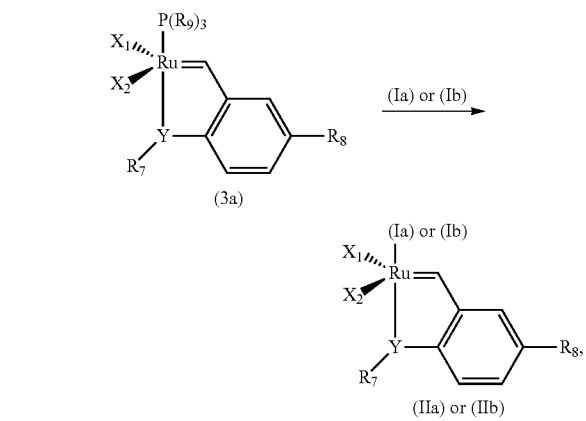

Scheme 2

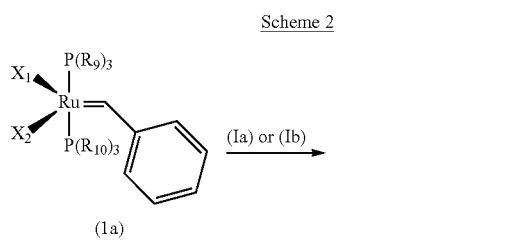

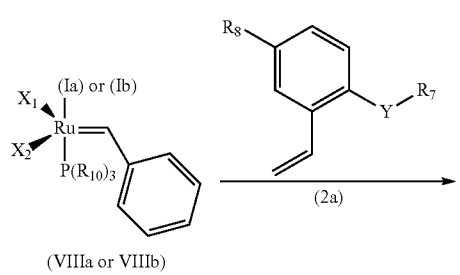

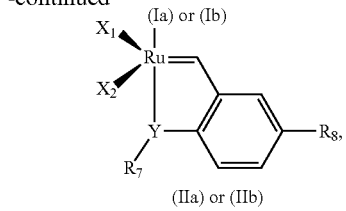

in which $R_7$ is selected from the group consisting of H, $C_1$-$C_{15}$ alkyl, $C_1$-$C_{15}$ alkoxy, $C_1$-$C_{15}$ thioether group, $C_1$-$C_{15}$ silyl, $C_1$-$C_{15}$ siloxy, $C_6$-$C_{15}$ aryl, $C_6$-$C_{15}$ aryloxy, $C_6$-$C_{15}$ heterocyclic aryl, $C_2$-$C_{15}$ heterocyclyl, sulfinyl, sulfonyl, $C_1$-$C_{15}$ carbonyl, $C_1$-$C_{15}$ ester group, $C_1$-$C_{15}$ amido, $C_1$-$C_{15}$ ureido, and $C_1$-$C_{15}$ sulfonamido;

$R_8$ is selected from the group consisting of H, F, Cl, Br, nitro, nitrile, formyl, $C_1$-$C_{15}$ aminosulfonyl ($R_2NSO_2$—), $C_1$-$C_{15}$ aminocarbonyl ($R_2NCO$—), $C_1$-$C_{15}$ carbonyl, $C_1$-$C_{15}$ ester group, $C_1$-$C_{15}$ amido, $C_1$-$C_{15}$ ureido or $C_1$-$C_{15}$ sulfonamido;

$R_9$ and $R_{10}$ are independently selected from the group consisting of butyl, cyclohexyl or phenyl;

$X_1$ and $X_2$ are Cl or RCOO—, in which R is $C_1$-$C_{20}$ alkyl;

Y is O, S, N or P.

wherein, the structure of formula (2a) is preferably:

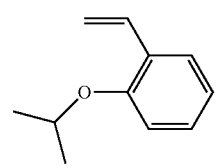

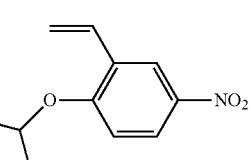

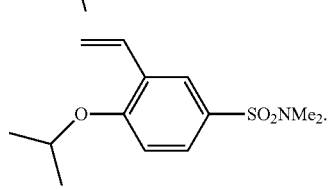

In addition, the ruthenium complex catalyst in the form of formula Ia or Ib according to the present invention can be directly prepared by the reaction of the direct precursor (IIa) or (IIb) having the structure NHC of formula Ia or Ib with the ruthenium complex of formula (1a), CuCl and the compound of formula (2a) under the protection of an inert gas.

Compared with the same kind of NHC structures in the prior art, the above-mentioned N-heterocyclic carbene (NHC) ligand and its corresponding ruthenium complex catalyst according to the present invention comprise a bulky group —CH($R_{3(4)}$)$_2$ at the ortho position of the benzene ring linkage to the nitrogen atom of N-heterocyclic ring in the NHC ligand, and at the same time, a strong electron-donating group —N($R_{1(2,5,6)}$)$_2$ is introduced. Thus, under the combined action of both of them, the catalytic activity of the catalyst can be significantly improved, and the performance of thermal stability is especially outstanding. The experimental results show that, in addition to having the catalytic performance and application field of the same kind of catalysts, the ruthenium complex catalyst of the present invention has a remarkable characteristic of being stable enough at 100° C., and thus as a highly efficient catalyst, the catalyst of the present invention can achieve satisfactory effect and have wide industrial application value in the fields of new materials, drug synthesis and the similar, such as olefin metathesis reaction and/or hydrogenation reaction including intramolecular ring-closing metathesis, intermolecular cross-olefin metathesis or olefin metathesis polymerization, which are difficult to complete by the same kind of catalysts in the prior art or on which their catalytic effects are poor.

Obviously, based on the above content of the present invention, according to the common technical knowledge and the conventional means in the field, without department from the above basic technical spirits, other various modifications, alternations, or changes can further be made.

With reference to the FIGURE and the specific way of the Examples, the above content of the present invention is further illustrated. But it should not be construed that the scope of the above subject matter of the present invention is only limited to the following examples. According to the common technical knowledge and the conventional means in the field, other various alternations or changes can further be made without department from the above basic technical spirits, that are all within the scope of the present invention

DESCRIPTION OF FIGURE

The FIGURE: The UV absorption spectrum of the ruthenium complex catalyst according to the present invention.

EXAMPLES

Example 1: Synthesis of Compound 8

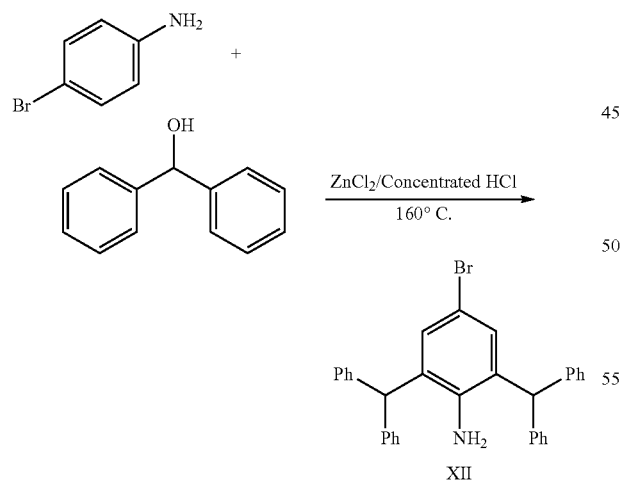

p-nitroaniline (40 g, 290 mmol, 1 eq) and diphenylmethanol (106 g, 580 mmol, 2 eq) were placed in a 1000 mL of single-neck flask, stirred and heated to 100° C. until the solid was completely dissolved, and then the solution of $ZnCl_2$ in concentrated HCl (19.4 g dissolved in 17.6 mL of 37% concentrated hydrochloric acid) was added dropwise. During the dropping process, white mist was released. After the addition was completed, the temperature was raised to 160° C. TLC detection indicated the point of starting material disappeared. Heating was stopped, and the temperature was reduced to room temperature. 300 mL of dichloromethane was added to dissolve the reaction. The organic phase was washed with $NH_4Cl$, and then with saturated saline. The organic phase was dried over anhydrous sodium sulfate, and then the solvent was removed to obtain 140 g of crude brown solid, which was crystallized in ethyl acetate/petroleum ether, followed by filtering and drying, to obtain 101 g of light yellow solid (8) with a yield of 74.3%.

$^1$H NMR (300 MHz, $CDCl_3$): δ 7.57 (s, 2H), 7.34-7.26 (m, 12H), 7.13-7.10 (m, 8H), 5.37 (s, 2H), 4.21 (s, 2H).

Example 2: Synthesis of Compound XIII

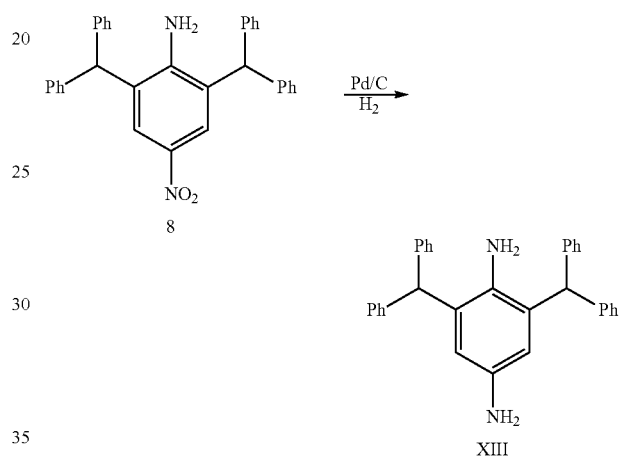

Starting compound 8 (100 g, 212.7 mmol) was dissolved in 1100 mL of chloroform and 580 mL of methanol, to which was added 10.0 g of Pd/C, and then hydrogen was purged after exchanging with hydrogen for several times. The reaction was heated to 45° C. The reaction was completed by monitoring with TLC. Pd/C was removed by filtration, to obtain light yellow liquid. The solvent was rotatory evaporated to dry, and then 200 mL of dichloromethane was added to dissolve the residue. 700 mL of petroleum ether was slowly added dropwise under stirring. After dropwise addition, pale yellow solid was precipitated, which was beaten for 1 h and then filtered. The filter cake was collected, to obtain light pink solid (XIII, 92.7 g), with a yield of 99%.

$^1$H NMR (300 MHz, $CD_3OD$): δ7.34-7.08 (m, 12H), 7.10-7.08 (m, 8H), 6.62 (s, 2H), 5.58 (s, 2H).

Example 3: Synthesis of Compound Va (Method I)

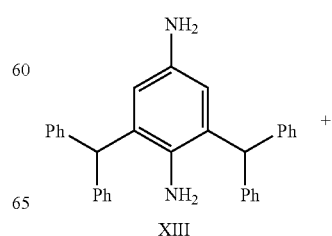

-continued

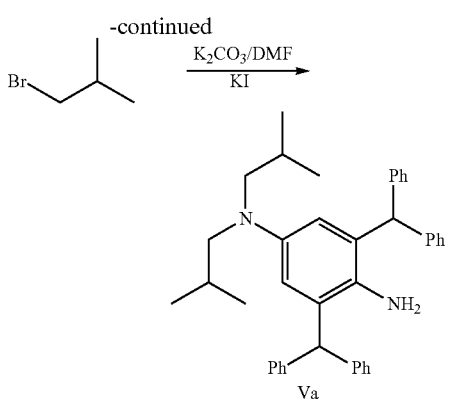

The starting material compound XIII (40.0 g, 91.2 mmol) was dissolved in 120 mL of N,N-dimethylformamide, to which were added K₂CO₃ (37.6 g, 272.1 mmol) and KI (4.5 g, 27.4 mmol). Bromoisobutane (31.8 g, 220.0 mmol) was added to the above solution, and then the reaction was heated to 100° C. TLC detection indicated the completion of the reaction. The reaction solution was extracted with ethyl acetate/water, and then the organic phase was washed with saturated brine, and dried over Na₂SO₄. The solvent was rotatory evaporated to dry to obtain brown oil, which was crystallized in ethyl acetate/petroleum ether and filtered, to obtain white solid (Va, 22.2 g), with a yield of 44.2%.

$^1$H NMR (300 MHz, CDCl₃): δ 7.30-7.19 (m, 12H), 7.18-7.11 (m, 8H), 5.86 (s, 2H), 5.50 (s, 2H), 2.91 (br, 2H), 2.66-2.64 (d, J=5.5 Hz, 4H), 1.60-1.56 (m, 2H), 0.62-0.60 (d, J=6.5 Hz, 12H).

Example 4: Synthesis of Compound XII

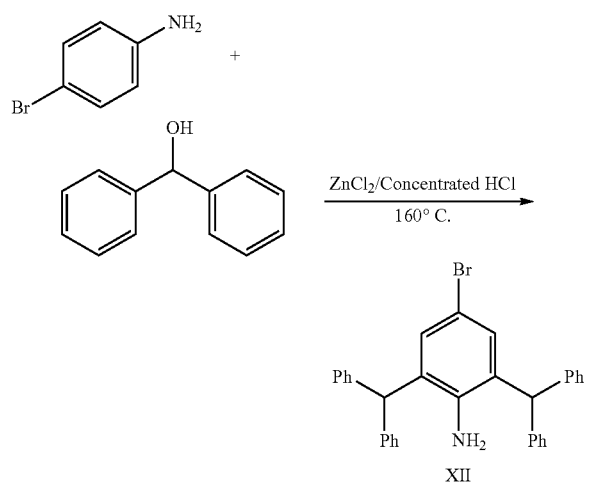

p-bromoaniline (5.0 g, 29 mmol) and diphenylmethanol (8.9 g, 48 mmol) were placed in a 250 mL single-neck flask, stirred and heated to 100° C. until the solid was completely dissolved, and then ZnCl₂/concentrated HCl solution was added dropwise. After addition, the reaction solution was heated to 160° C., and allowed to react for 2 h. The solution was cooled to room temperature, and then 100 mL of dichloromethane was added for dissolution. The organic phase was successively washed with NH₄Cl and a saturated saline solution, and then dried over anhydrous sodium sulfate. The solvent was removed, and the residue was beaten in ethyl acetate, filtered and dried to obtain 6.0 g of light yellow solid with a yield of 50.0%.

$^1$H NMR (300 MHz, CDCl₃) δ 7.35-7.20 (m, 12H), 7.14-7.03 (m, 8H), 6.69 (s, 2H), 5.40 (s, 2H).

Example 5: Synthesis of Compound Va (Method II)

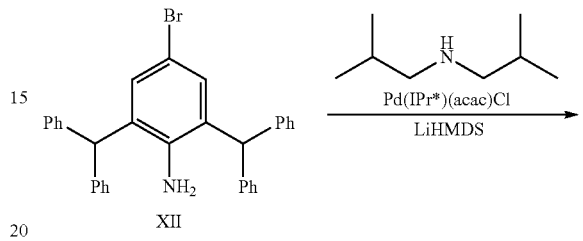

Compound XII (1.0 g, 1.98 mmol) was mixed with diisobutylamine (333 mg, 2.58 mmol) in an inert gas, and then moved into a reaction tube, to which were successively added Pd(IPr*)(acac)Cl (12.7 mg, 0.00595 mmol) and LiHMDS (lithium hexamethyldisilazide) (2.38 mmol), and then 2 mL of 1,4-dioxane was added to dissolve the reaction. The reaction solution was heated to 110° C. and allowed to react for 3 h. After completion of the reaction, the reaction solution was sequentially washed with 20 mL of water and 10 mL of dichloromethane. The dichloromethane phase was collected, washed with saturated saline, and dried over anhydrous sodium sulfate. Dichloromethane was removed, and the residue was purified by column chromatography, to give 0.48 g of pale pink solid with a yield of 55.1%.

Example 6: Synthesis of Compound VI

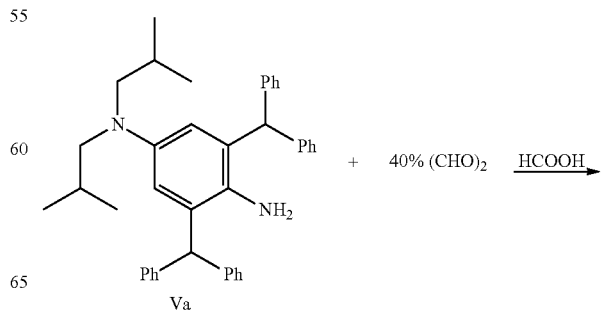

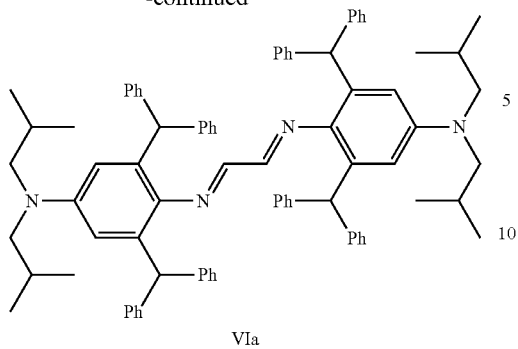

VIa

The starting material compound Va (20.0 g, 36.2 mmol) was dissolved in 120 mL of chloroform, to which were added 400 mL of methyl t-butyl ether and 500 mL of absolute ethyl alcohol, and then the reaction solution was heated to 58° C. Formic acid (410 μL, 10.9 mmol) was added, followed by drop addition of glyoxal (5.4 mL, 47.0 mmol). The reaction was detected with TLC until the point of raw material disappeared. The reaction solution was filtered to obtain an orange solid, which was beaten in a mixed solvent of petroleum ether/ethyl acetate. After filtration, 16.0 g of orange solid (VIa) was obtained with a yield of 78.5%.

$^1$H NMR (300 MHz, CDCl$_3$) δ 7.31 (d, J=4.3 Hz, 2H), 7.20 (dq, J=14.2, 7.0 Hz, 13H), 7.04 (d, J=7.1 Hz, 8H), 6.07 (s, 2H), 5.39 (s, 2H), 2.81 (d, J=6.9 Hz, 4H), 1.71-1.54 (m, 4H), 0.68 (d, J=6.6 Hz, 12H).

Example 7: Synthesis of Compound IIIaa

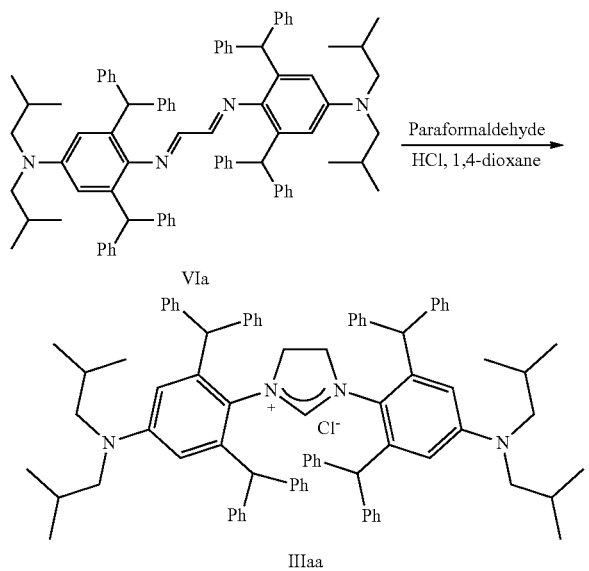

IIIaa

The starting compound VIa (10.0 g, 8.87 mmol) was dissolved in trichloromethane (160 mL), and then the solution was heated to 60° C., to which was added paraformaldehyde (0.8 g, 26.60 mmol). Then, the newly prepared solution of 4 M HCl (4.9 mL) was slowly added dropwise to the reaction solution, and the reaction was completed by TLC detection. The reaction solution was rotatory evaporated to dry, and the residue was crystallized in ethyl acetate/petroleum ether. After filtration, 5.93 g of white solid (IIIaa) was obtained, with a yield of 56.3%.

$^1$H NMR (300 MHz, CDCl$_3$) δ 7.21 (d, J=28.3 Hz, 34H), 6.86 (s, 8H), 5.97 (s, 4H), 5.44-5.32 (m, 2H), 5.30 (s, 1H), 5.18 (s, 4H), 2.76 (s, 8H), 1.58 (s, 14H), 0.62 (d, J=5.7 Hz, 23H).

Example 8: Synthesis of Compound VIIa

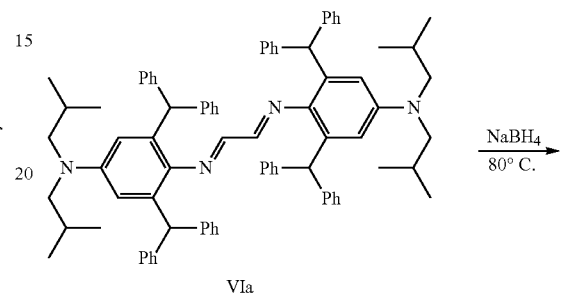

VIa

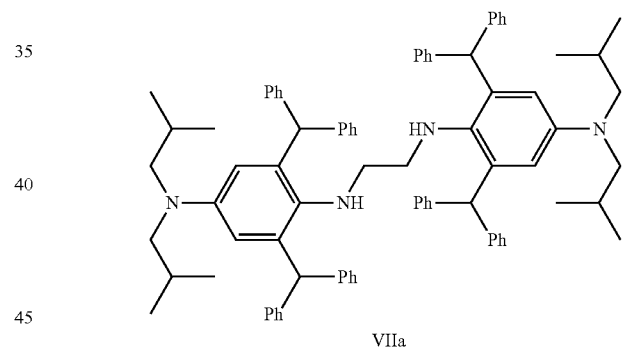

VIIa

Imine (10.00 g, 8.87 mmol) was put into 500 mL of single-neck bottle, and then 500 mL of THF was added, to which was slowly added sodium borohydride (3.35 g, 88.68 mmol) in an ice bath. Then, the reaction solution was refluxed at 80° C. under argon protection, and allowed to react for 10 h. The reaction was completed by monitoring with TLC. After completion of the reaction, 1 M HCl solution was drop added to the reaction solution in an ice bath, until no bubbles emerged, and then the reaction solution was warmed to room temperature. The reaction solution was extracted with dichloromethane, and then the solvent was rotatory evaporated to dry. The residue was purified by column chromatography, to provide 6.42 g of yellow solid, with a yield of 64.0%.

$^1$H NMR (300 MHz, CDCl$_3$) δ 7.27-7.11 (m, 6H), 7.02 (d, J=7.2 Hz, 4H), 5.98 (s, 1H), 5.75 (s, 1H), 2.77 (d, J=6.8 Hz, 2H), 2.31 (s, 1H), 1.58 (dt, J=13.0, 6.5 Hz, 1H), 0.65 (d, J=6.6 Hz, 6H).

Example 9: Synthesis of Compound IIIba

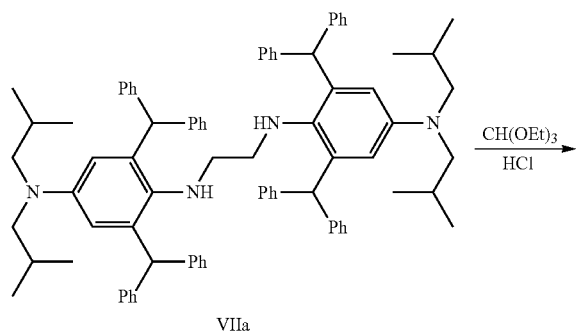

VIIa

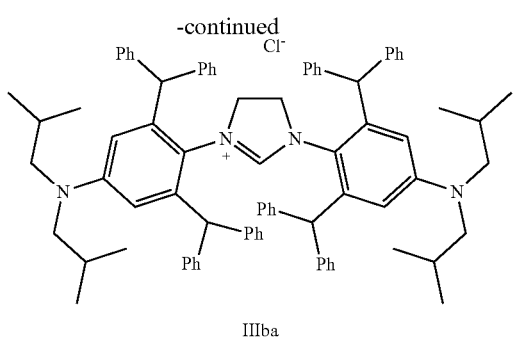

IIIba

The raw material VIIa (6.00 g, 5.30 mmol) was dissolved in triethyl orthoformate (150 mL), to which was added the solution of 4 M HCl (26.51 mmol) in 1,4-dioxane in drops at 60° C. The solution changed from orange to black, and then nitrogen was introduced. The reaction solution was heated to 100° C., and became yellow and clear. The solution was further heated to 140° C. and allowed to react for 1.5 h. TLC detection indicated the disappearance of raw material point, and then the reaction was stopped. The reaction solution was cooled. The solvent was removed. The residue was purified by column chromatography, to provide 1.95 g of light yellow solid, with a yield of 31.2%.

$^1$H NMR (300 MHz, CDCl$_3$) δ 10.82 (s, 1H), 7.35-7.17 (m, 32H), 7.14-7.04 (m, 8H), 5.98 (s, 4H), 5.79 (s, 4H), 2.78 (d, J=7.0 Hz, 8H), 2.55 (s, 4H), 1.62-1.45 (m, 4H), 0.64 (d, J=6.6 Hz 24H).

Example 10: Synthesis of Compound IIaa1

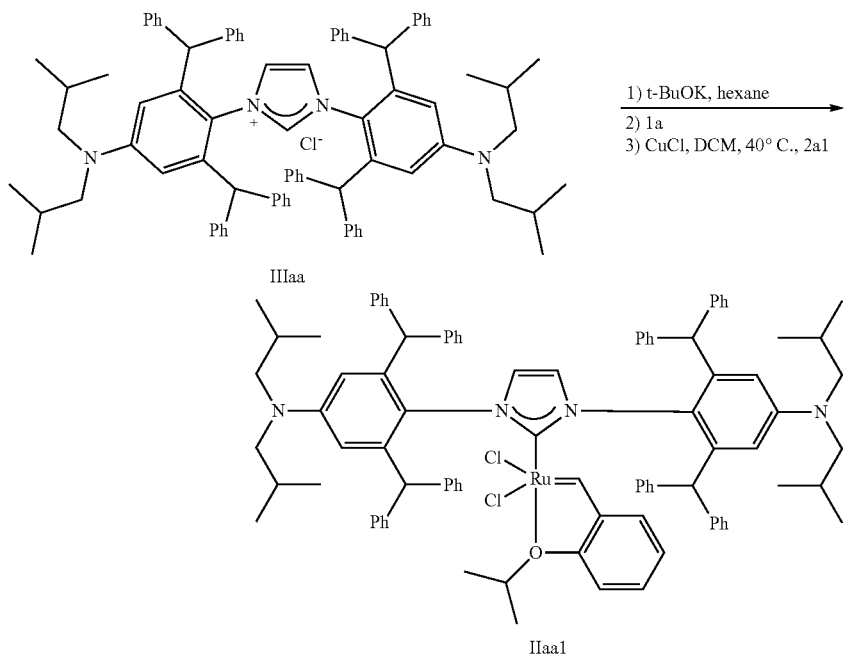

The first-generation Grubbs catalyst 1a (1.22 mmol) was added to 100 mL of Schlenk flask under anhydrous and anaerobic conditions, to which were added compound IIIaa (2858 mg, 2.43 mmol) and potassium t-butoxide (286 mg, 2.55 mmol), and then 50 mL of n-hexane was added. After reacting for h at 60° C. under stirring, the reaction was completed by monitoring with TLC. After completion of the reaction, n-hexane was removed under reduced pressure. The intermediate obtained in the previous step was dissolved in 40 mL of dichloromethane, to which was added cuprous chloride (300 mg, 1.42 mmol), and then the reaction solution was stirred for 5 min. Then, compound 2a1 (296 mg, 1.82 mmol) was added to the reaction flask, and the reaction solution was heated to 40° C. The reaction was completed by TLC detection. After completion of the reaction, the reaction was purified by column chromatography, to provide 574 mg of IIaa1 as light green solid, with a yield of 32.3%.

$^1$H NMR (400 MHz, CDCl$_3$) δ 17.14 (s, 1H), 7.53 (s, 6H), 7.24-6.76 (m, 34H), 6.67 (s, 4H), 6.20 (d, J=20.9 Hz, 4H), 6.00 (s, 2H), 5.84 (s, 2H), 5.05 (m, 1H), 2.89 (d, 8H), 1.82-1.66 (m, 4H), 1.26 (d, 6H), 0.67 (d, 24H).

Example 11: Synthesis of Compound IIaa2

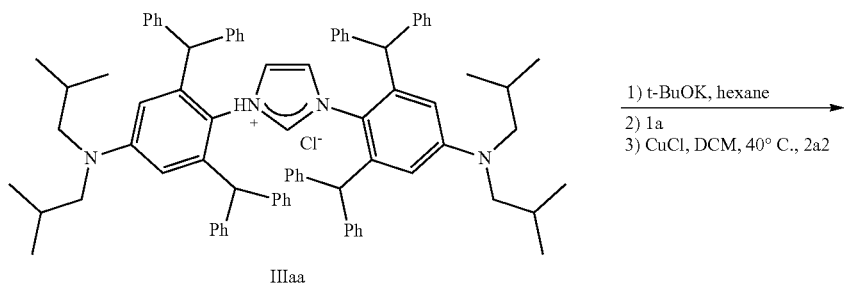

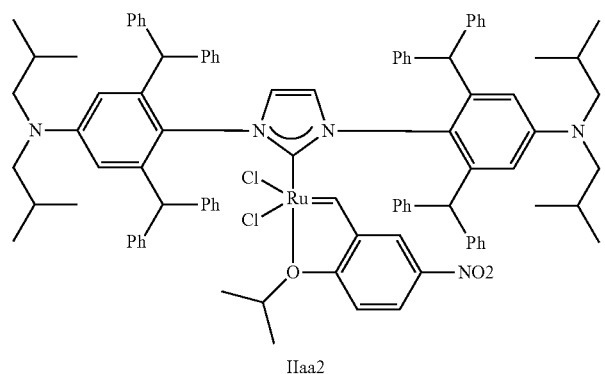

The first-generation Grubbs catalyst 1a (1.22 mmol) was added to 100 mL of Schlenk flask under anhydrous and anaerobic conditions, to which were added compound IIIaa (2858 mg, 2.43 mmol) and potassium t-butoxide (286 mg, 2.55 mmol), and then 50 mL of n-hexane was added. After reacting for 5 h at 60° C. under stirring, the reaction was completed by monitoring with TLC. After completion of the reaction, n-hexane was removed under reduced pressure. The intermediate obtained in the previous step was dissolved in 40 mL of dichloromethane, to which was added cuprous chloride (300 mg, 1.42 mmol), and then the reaction solution was stirred for 5 min. Then, compound 2a2 (378 mg, 1.82 mmol) was added to the reaction flask, and the reaction solution was heated to 40° C. The reaction was completed by TLC detection. After completion of the reaction, the reaction was purified by column chromatography, to provide 561 mg of IIaa2 as light green solid, with a yield of 30.7%.

$^1$H NMR (400 MHz, CDCl$_3$) δ 17.22 (s, 1H), 7.78 (d, J=2.3 Hz, 1H), 7.49 (d, J=5.4 Hz, 4H), 7.16-6.89 (m, 34H), 6.66 (s, 4H), 6.24 (s, 4H), 5.93 (s, 2H), 5.77 (s, 2H), 5.16 (m, 1H), 2.91 (d, J=8.8 Hz, 8H), 1.88-1.65 (m, 4H), 1.28 (m, 6H), 0.67 (d, 24H).

Example 12: Synthesis of Compound IIaa3

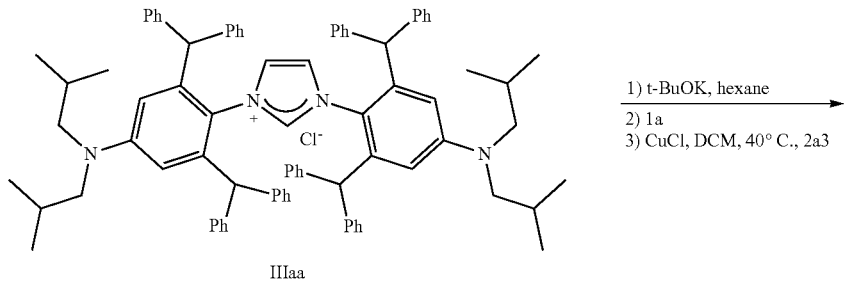

-continued

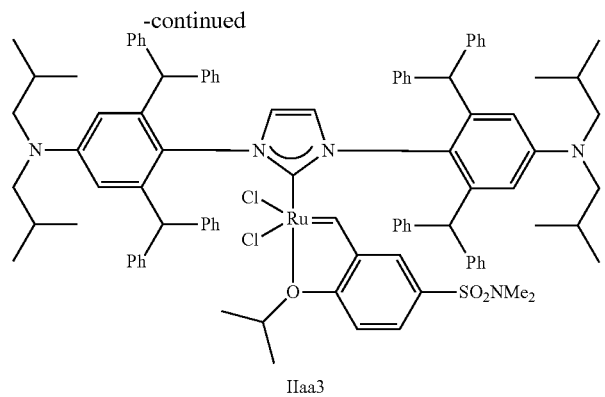

IIaa3

The first-generation Grubbs catalyst 1a (1.22 mmol) was added to 100 mL of Schlenk flask under anhydrous and anaerobic conditions, to which were added compound Mao (2858 mg, 2.43 mmol) and potassium t-butoxide (286 mg, 2.55 mmol), and then 50 mL of n-hexane was added. After reacting for 5 h at 60° C. under stirring, the reaction was completed by monitoring with TLC. After completion of the reaction, n-hexane was removed under reduced pressure. The intermediate obtained in the previous step was dissolved in 40 mL of dichloromethane, to which was added cuprous chloride (300 mg, 1.42 mmol), and then the reaction solution was stirred for 5 min. Then, compound 2a3 (378 mg, 1.82 mmol) was added to the reaction flask, and the reaction solution was heated to 40° C. The reaction was completed by TLC detection. After completion of the reaction, the reaction was purified by column chromatography, to provide 550 mg of IIaa3 as light green solid, with a yield of 28.9%.

$^1$H NMR (400 MHz, CDCl$_3$) δ 17.28 (s, 1H), 8.08-7.95 (m, 1H), 7.50 (d, J=7.1 Hz, 4H), 7.31 (d, J=1.9 Hz, 1H), 7.23-7.06 (m, 14H), 7.00 (s, 10H), 6.90 (s, 10H), 6.65 (s, 4H), 6.25 (d, J=10.7 Hz, 4H), 5.95 (s, 2H), 5.79 (s, 2H), 5.15 (m, J=12.2, 6.1 Hz, 1H), 2.88 (d, J=6.9 Hz, 8H), 1.81-1.66 (m, 4H), 1.27 (d, 6H), 0.67 (d, 24H).

Example 13: Synthesis of Compound IIBa1

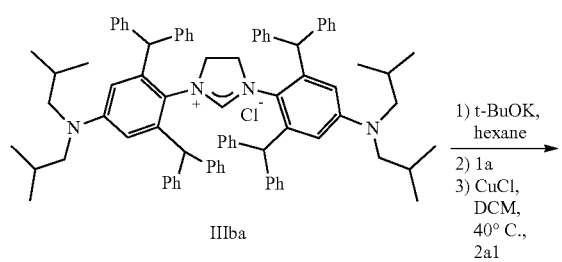

IIIba 1) t-BuOK, hexane
2) 1a
3) CuCl, DCM, 40° C., 2a1

-continued

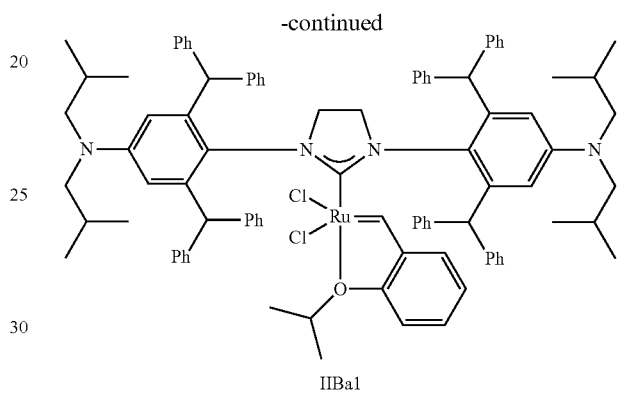

IIBa1

The first-generation Grubbs catalyst 1a (1.22 mmol) was added to 100 mL of Schlenk flask under anhydrous and anaerobic conditions, to which were added compound IIIba (2863 mg, 2.43 mmol) and potassium t-butoxide (477 mg, 4.25 mmol), and then 50 mL of n-hexane was added. After reacting for 5 h at 60° C. under stirring, the reaction was completed by monitoring with TLC. After completion of the reaction, n-hexane was removed under reduced pressure. The intermediate obtained in the previous step was dissolved in 40 mL of dichloromethane, to which was added cuprous chloride (300 mg, 1.42 mmol), and then the reaction solution was stirred for 5 min. Then, compound 2a1 (296 mg, 1.82 mmol) was added to the reaction flask, and the reaction solution was heated to 40° C. The reaction was completed by TLC detection. After completion of the reaction, the reaction was purified by column chromatography, to provide 568 mg of IIba1 as light green solid, with a yield of 32.0%.

$^1$H NMR (400 MHz, CDCl$_3$) δ 17.45 (s, 1H), 7.62-7.05 (m, 40H), 6.72 (s, 4H), 6.25 (s, 4H), 6.07 (s, 4H), 5.05 (m, 1H), 2.89 (d, 8H), 2.64 (s, 4H), 1.82-1.66 (m, 4H), 1.26 (d, 6H), 0.67 (d, 24H).

Example 14: Experiments on the Thermal Stability of Catalysts

The current Ru complex catalyst is very easy to decompose at high temperature, and the lack of stability is one of the defects of Ru complex catalyst products at present. The thermal stability of Ru complex catalyst according to the present invention was tested by ultraviolet absorption (UV) with reference to the method in literature (Plenio et al., J. Am. Chem. Soc., 2012, 134(2): 1104-1114). 25 mL solution of catalyst IIaa1 in toluene was prepared at a concentration of $2.0\times10^{-5}$ mol/L. Firstly, 3 mL solution of catalyst IIaa1 in toluene was taken out, and then its UV-Vis absorption was detected at room temperature. Then, 3 mL solution of catalyst IIaa1 in toluene was collected and heated at 50° C., 70° C., 90° C. and 100° C. for 4 h under inert gas, respectively, and the change of characteristic absorption peak was measured by UV-Vis. The UV absorption spectra of catalyst IIaa1 after heating at different temperatures were shown in the FIGURE, indicating satisfactory thermal stability.

Example 15: Synthesis of Compound Vb

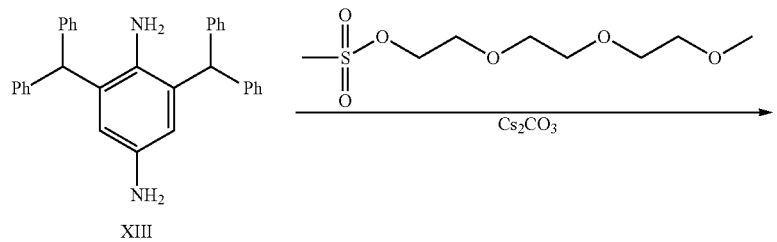

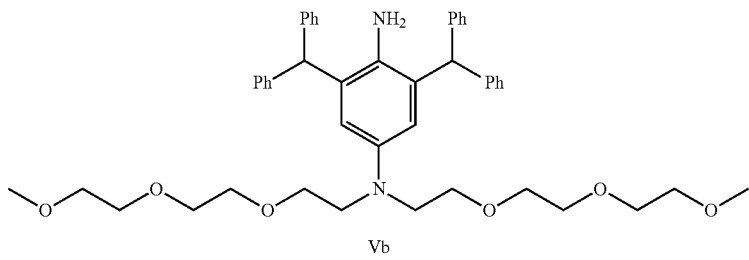

Compound XIII (20.00 g, 45.4 mmol) was placed in 500 mL of round bottom flask, and then 300 mL of acetonitrile was added, followed by addition of polyethylene glycol monomethyl ether mesylate (22.0 g, 90.8 mmol) under stirring. Then, cesium carbonate (29.6 g, 90.8 mmol) was added, and the reaction solution was heated to 82° C. After reacting for 10 h, polyethylene glycol monomethyl ether mesylate (22.0 g, 90.8 mmol) and cesium carbonate (29.6 g, 90.8 mmol) were further added. The resultant solution was allowed to react for further 10 h, and then additional polyethylene glycol monomethyl ether mesylate (22.0 g, 90.8 mmol) and cesium carbonate (29.6 g, 90.8 mmol) were added. The mixture was allowed to react until the disappearance of the starting material. The inorganic salt was removed by filtration, and the solvent was evaporated. The residue was purified by column chromatography, to obtain 20.86 g of brownish oil, with a yield of 62.7%.

Example 16: Synthesis of Compound VIb

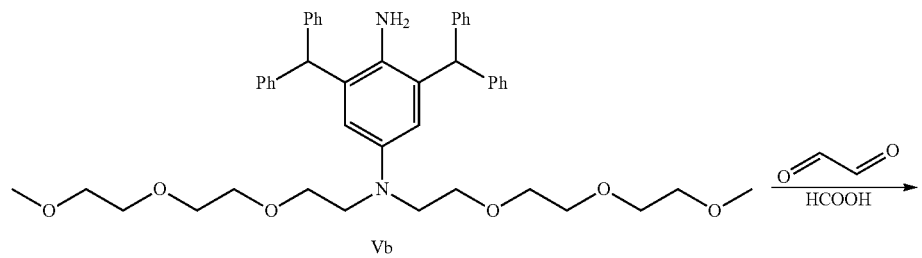

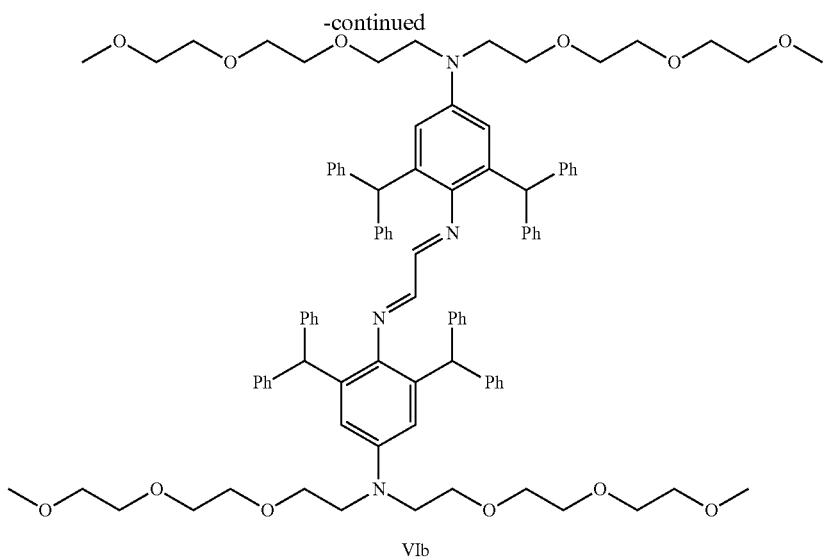

VIb

The raw material (1.00 g, 1.37 mmol) was dissolved in 30 mL of dichloromethane, and then anhydrous magnesium sulfate (1.20 g) was added to the reaction solution, followed by addition of 40% glyoxal solution (230 μL). Formic acid (0.5 mL) was added to the reaction solution, and the resultant mixture was allowed to react at room temperature. During the reaction, 1.2 equivalent of glyoxal was added 3 times, together with addition of formic acid (0.5 mL) and 5 equivalents of anhydrous magnesium sulfate. The reaction was stopped after 72 h. The reaction solution was passed through celite to remove the inorganic salts, and then the solvent was evaporated. The residue was purified by column chromatography, to obtain orange-yellow solid, with a yield of 53.0%.

$^1$H NMR (300 MHz, CDCl$_3$) δ 7.15 (td, J=14.1, 6.9 Hz, 7H), 6.99 (d, J=6.8 Hz, 4H), 6.12 (s, 1H), 5.32 (s, 1H), 3.57 (dd, J=6.0, 3.1 Hz, 2H), 3.52 (dd, J=5.7, 3.5 Hz, 4H), 3.41-3.33 (m, 6H), 3.23 (s, 3H).

Example 17: Synthesis of Compound IIIab

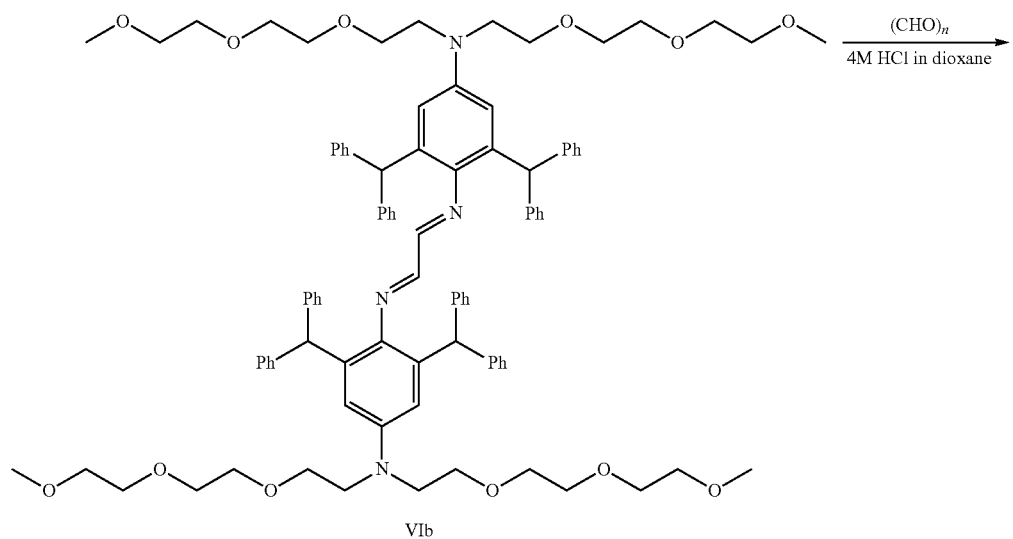

VIb

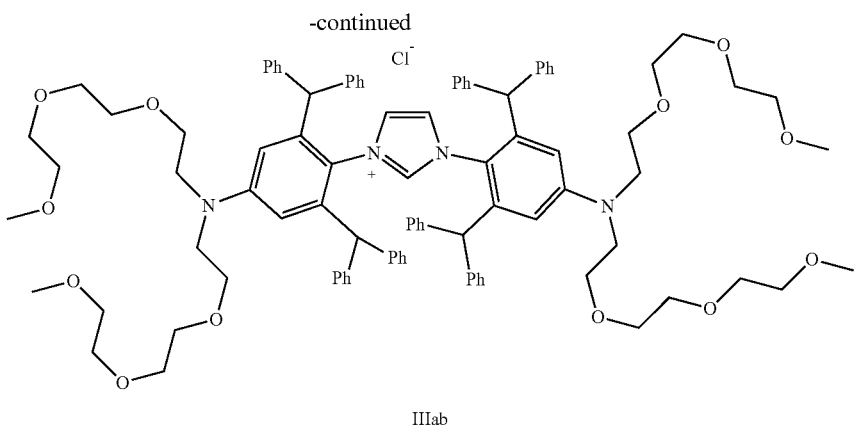

IIIab

The imine raw material (50.0 mg, 0.033 mmol) was dissolved in CHCl₃ (1.5 mL), and the solution was heated to 60° C., to which was then added paraformaldehyde (3.0 mg, 0.099 mmol). Then, the solution of 4 M HCl in 1,4-dioxane (0.1 mL) was added dropwise. The resultant solution changed from orange-red to brown-black, and after about 2 min, the solution gradually became brown-yellow. TLC was used to detect the reaction until the raw material disappeared, and then the reaction was stopped. The reaction solution was evaporated, and the residue was purified by column chromatography, to provide 29 mg of light gray-white colloidal product, with a yield of 56.2%.

$^1$H NMR (300 MHz, CDCl₃) δ 11.92 (s, 1H), 7.33-7.21 (m, 10H), 7.16 (t, J=8.1 Hz, 22H), 6.86 (s, 8H), 6.08 (s, 4H), 5.41 (s, 2H), 5.19 (s, 4H), 3.62-3.55 (m, 8H), 3.55-3.46 (m, 16H), 3.37 (d, J=5.1 Hz, 24H), 3.28-3.14 (s, 12H).

Example 18: Synthesis of Compound Vc

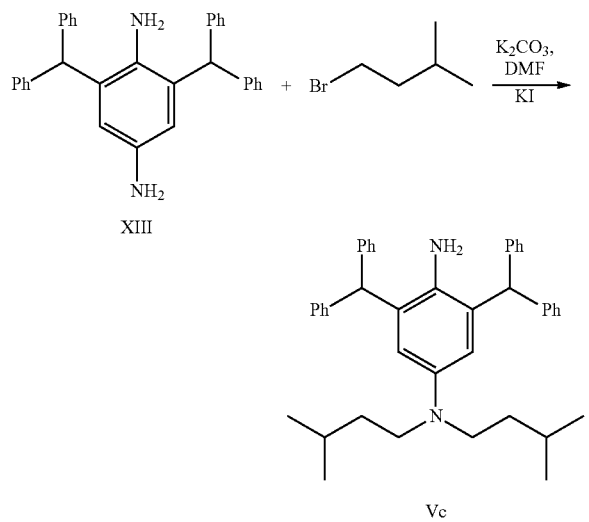

Compound XIII (17.0 g, 38.6 mmol) was dissolved in DMF (60 mL), to which were added K₂CO₃ (17.5 g, 96.5 mmol) and KI (1.7 g, 10.0 mmol). Bromoisopentane (1.7 g, 10.0 mmol) was drop added into the above solution, and then the mixture was heated to 100° C. and allowed to react for 4 h. The reaction was stopped. The reaction solution was extracted with 300 mL of ethyl acetate and 600 mL of water. Finally, the organic phase was washed with saturated saline, and subjected to column chromatography. The solvent was evaporated to dry, to obtain milky white solid (9.50 g, 16.36 mmol), with a yield of 42.2%.

Example 19: Synthesis of Compound VIc

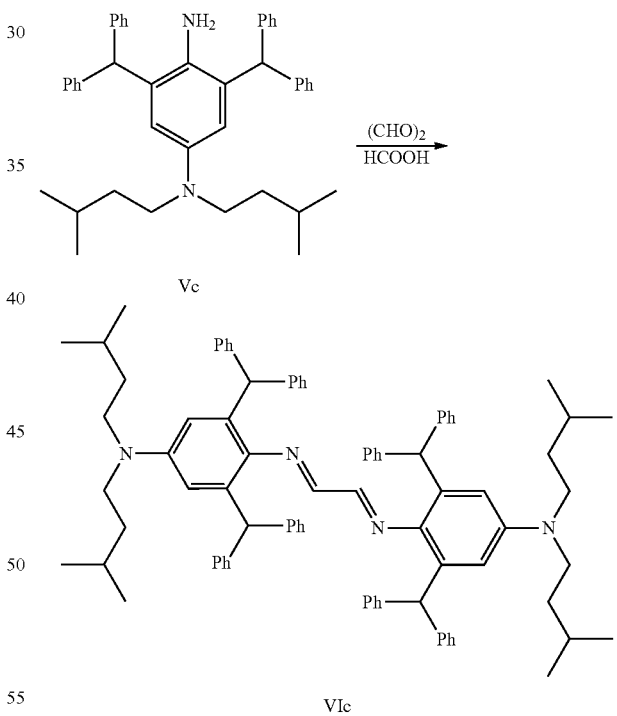

The raw material (5.00 g, 8.62 mmol) of the product from the previous step was dissolved in methyl t-butyl ether (100 mL) and EtOH (100 mL), to which was added 40% glyoxal solution (1.63 g, 11.19 mmol) dropwise, and then formic acid (155 mg, 2.58 mmol) was added dropwise into the reaction solution. The mixture was heated to 60° C. The reaction solution gradually turned orange, and orange solids precipitated after about 30 min. After 5 h of reaction, 80 mg formic acid and 0.8 equivalent of 40% glyoxal were added. The resultant mixture was allowed to react for 10 min, and then the reaction was stopped. The solution was filtered to obtain orange-yellow solid, which was beaten in the mixed solvent of petroleum ether/ethyl acetate, to obtain 2.70 g of orange-yellow solid, with a yield of 53.1%.

Example 20: Synthesis of Compound IIIac

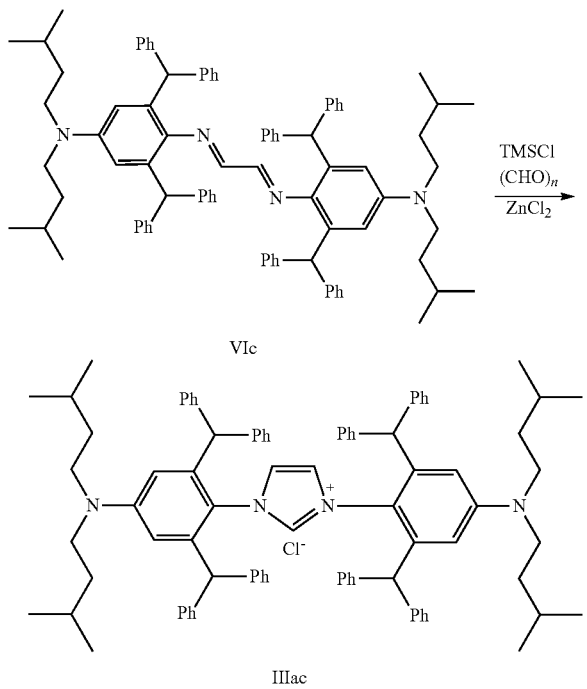

VIc (100.0 mg, 0.083 mmol) was dissolved in anhydrous THF (2 mL), to which was added $ZnCl_2$ (12.0 mg, 0.100 mmol) under stirring, and then the solution was heated to 45° C. and stirred for 5 min. Paraformaldehyde (2.6 mg, 0.100 mmol) was added to the reaction solution, and the resultant solution was heated to 70° C. and stirred for 5 min. TMSCl (9.6 mg, 0.100 mmol) was dissolved in anhydrous THF (1 mL), and added to the reaction solution dropwise. After addition, the mixture was reacted at 70° C. The reaction was stopped after heating for 6 h. Tetrahydrofuran was evaporated, and the residue was crystallized in dichloromethane/n-pentane, to obtain 70 mg of product as brown solid, with a yield of 66.4%.

$^1$H NMR (300 MHz, $CDCl_3$) δ 10.73 (s, 1H), 7.29-7.21 (m, 10H), 7.18 (m, 16H), 7.08 (d, J=7.3 Hz, 8H), 6.91-6.83 (m, 6H), 6.00 (s, 4H), 5.50 (d, J=1.2 Hz, 2H), 5.10 (s, 4H), 2.98-2.83 (m, 8H), 1.31-1.16 (m, 8H), 1.08 (d, J=8.4 Hz, 4H), 0.69 (d, J=6.5 Hz, 24H).

Example 21: Synthesis of Compound Vd

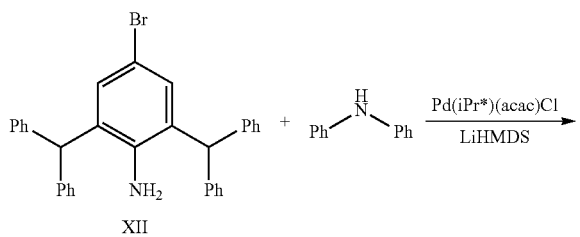

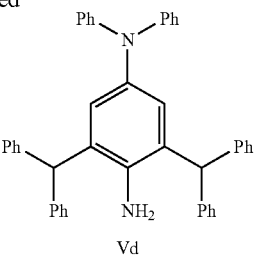

Compound XII (1.0 g, 1.98 mmol) was mixed with diphenylamine (437 mg, 2.58 mmol) in an inert gas, and then moved into a reaction tube, to which were successively added Pd(IPr*)(acac)Cl (12.7 mg, 0.00595 mmol) and LiHMDS (lithium hexamethyldisilazide) (2.38 mmol), and then 2 mL of 1,4-dioxane was added to dissolve the reaction. The reaction solution was heated to 110° C. and allowed to react for 3 h. After completion of the reaction, the reaction solution was sequentially washed with 20 mL of water and 10 mL of dichloromethane. The dichloromethane phase was collected, washed with saturated saline, and dried over anhydrous sodium sulfate. Dichloromethane was removed, and the residue was purified by column chromatography, to give 624 mg of pale pink solid, with a yield of 53.0%.

Example 22: Synthesis of Compound VId

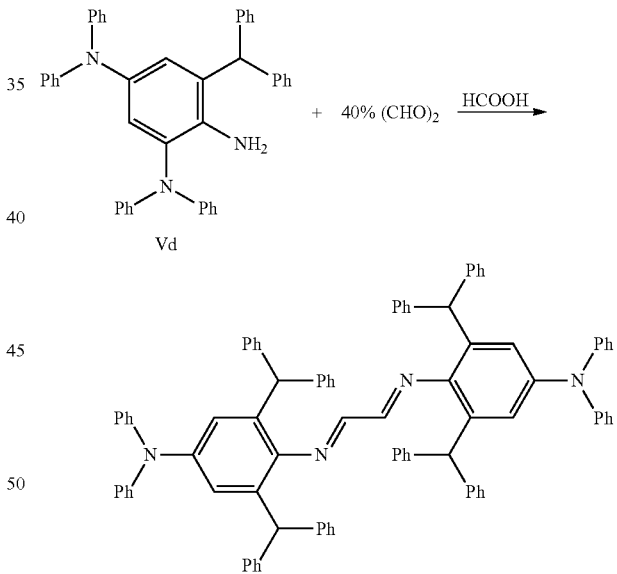

Compound Va (10.0 g, 16.8 mmol) of the product from the previous step was dissolved in 60 mL of chloroform, to which were added 200 mL of methyl t-butyl ether and 250 mL of absolute ethanol, and then the reaction solution was heated to 58° C. Formic acid (190 μL, 5.1 mmol) was added, followed by drop addition of glyoxal (2.5 mL, 21.9 mmol). The reaction was detected with TLC until the point of raw material disappeared. The reaction solution was filtered to obtain an orange solid, which was crystallized in a mixed solvent of petroleum ether/ethyl acetate. After filtration, 9.37 g of orange solid (VId) was obtained, with a yield of 92%.

Example 23: Synthesis of Compound IIIad

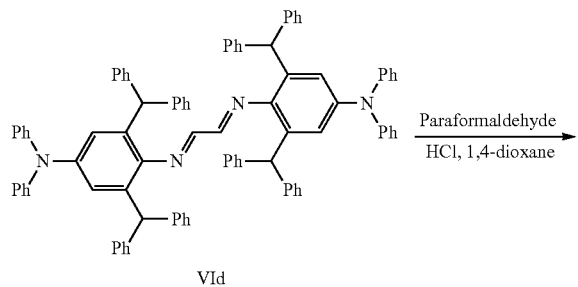

VId

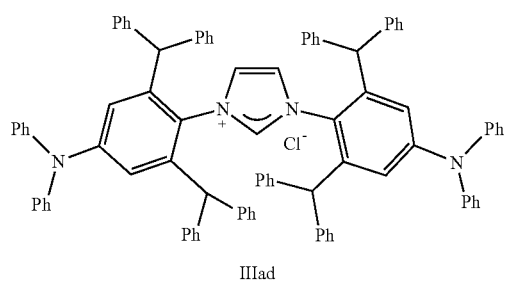

IIIad

The starting compound VId (5.0 g, 4.14 mmol) was dissolved in trichloromethane (100 mL), and then the solution was heated to 60° C., to which was added paraformaldehyde (373 mg, 12.4 mmol). Then, the newly prepared solution of 4 M HCl (2.3 mL) was slowly added dropwise to the reaction solution, and the reaction was completed by TLC detection. The reaction solution was rotatory evaporated to dry, and the residue was crystallized in ethyl acetate/petroleum ether. After filtration, 2.55 g of white solid (IIIad) was obtained, with a yield of 52.0%.

NMR (300 MHz, CDCl$_3$) δ 12.72 (m, 1H), 7.10 (dd, J=13.7, 7.5 Hz, 40H), 6.95 (t, J=7.8 Hz, 12H), 6.78 (d, J=6.6 Hz, 8H), 6.50 (s, 4H), 5.55 (s, 2H), 5.16 (s, 4H).

The following are examples of application of the ruthenium complex catalyst according to the present invention in the olefin metathesis.

Example 24: Preparation of dimethyl 3-cyclopentene-1,1-dicarboxylate 12

Dimethyl 3-cyclopentene-1,1-dicarboxylate (12) is an intermediate in the synthesis of 3-cyclopentene-1-carboxylic acid and its derivatives, the latter being mainly used in carbocyclic nucleosides, prostaglandins and other common important drugs. Dimethyl 3-cyclopentene-1,1-dicarboxylate (12) was prepared from dimethyl diallylmalonate (11), to test the catalytic activity of the ruthenium complex catalysts (IIa and IIb) synthesized in the example for the intramolecular olefin metathesis reaction, and the activity was compared with that of the second-generation H-G catalyst (H-G II).

Preparation of dimethyl 3-cyclopentene-1,1-dicarboxylate 12

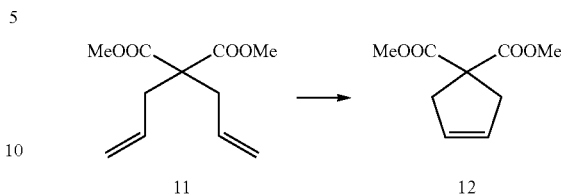

Intramolecular cyclization metathesis reaction of olefins: 1.0 g of dimethyl diallylmalonate was dissolved in 2 mL of n-heptane. Nitrogen was introduced, and the resultant mixture was stirred at room temperature for 20 min; different amount of catalyst in n-heptane (1 mL) solution was transferred into a reactor. The mixture was heated to 100° C., and reacted for 120 min. The conversion rate was calculated or tested, and the results are shown in Table 1 below.

Products of intramolecular cyclization of olefins (12): $^1$H NMR (300 MHz, CDCl$_3$): δ (ppm)=5.61 (2H, s), 3.74 (6H, s), 3.02 (4H, s).

TABLE 1

The results of conversion rate.

| No. | Type of catalyst | Amount of catalyst | Conversion rate (%) |
|---|---|---|---|
| 1 | H-G II | 1 mol % | 99 |
| 7 | H-G II | 0.03 mol % | 97 |
| 3 | II aa1 (Example 10) | 0.03 mol % | 99 |
| 4 | II aa2 (Example 11) | 0.03 mol % | 99 |
| 5 | II aa3 (Example 12) | 0.03 mol % | 99 |
| 6 | II ba1 (Example 13) | 0.03 mol % | 99 |

As shown in the above effect examples, for the intramolecular olefin metathesis of dimethyl diallylmalonate (11), the sterically hindered, electron-rich NHC catalyst of the present invention has significantly better catalytic activity than the same kind of H-G II catalyst.

Macrocyclic compounds are widely used in drugs, especially antiviral drugs. However, olefin metathesis is a simple method to construct macrocyclic compounds. The intermediate (16) of anti-hepatitis C drug Danoprevir Sodium was prepared by intramolecular olefin metathesis of an olefin intermediate compound (15) using a second-generation H-G catalyst (U.S. Pat. No. 8,299,021B2, yield 52%) and a Zhan-1B catalyst (WO2011091757), respectively. The activity of the ruthenium complex catalyst of the present invention can be further demonstrated by performing an intramolecular ring-closing reaction of the intermediate compound (15).

The preparation route of the intermediate (16) of Danoprevir Sodium was as follows:

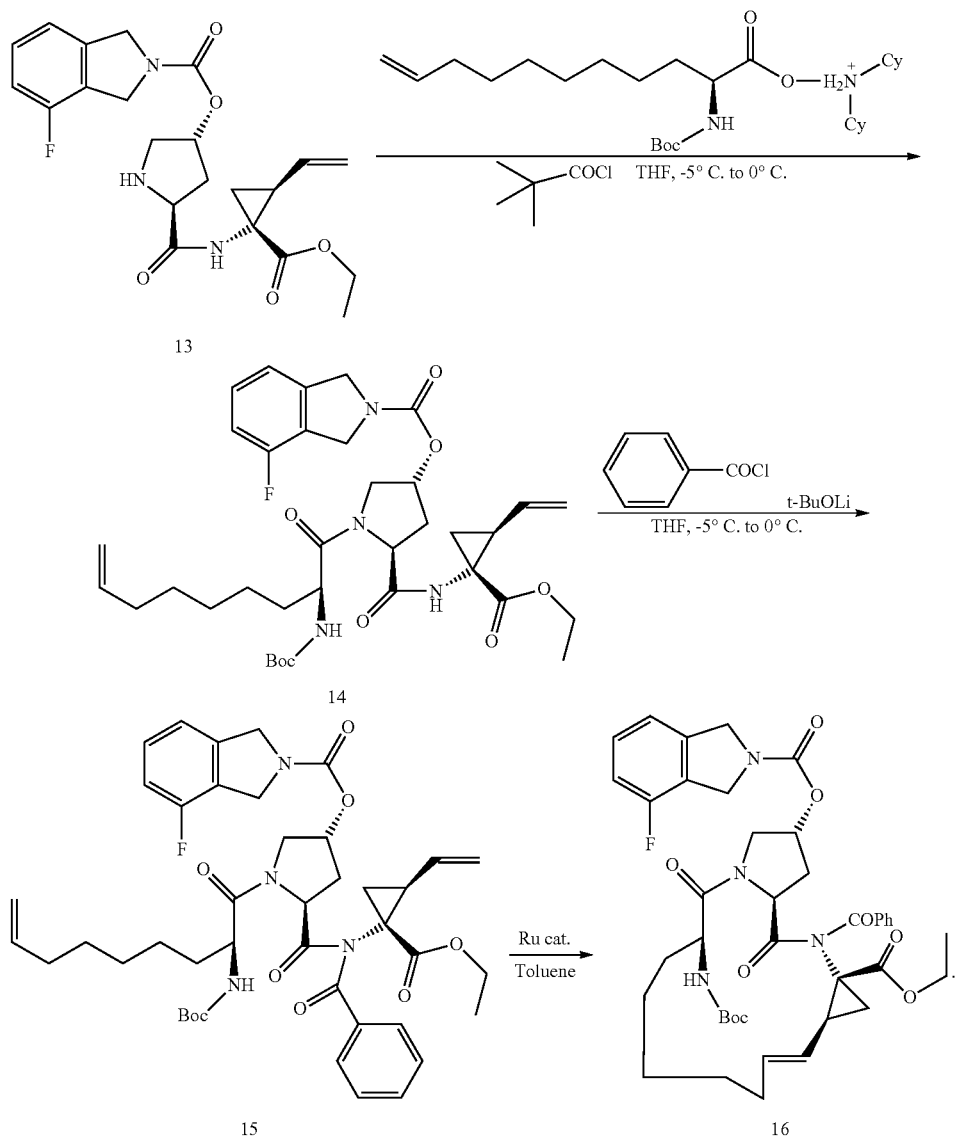

Example 25: Preparation of Intermediate Compound 14

Under the protection of inert gas, the reaction system was cooled to about −5° C., and the substrate ethyl (S)-2-((t-butoxycarbonyl)amino)non-8-enoate (13.8 g, 30.5 mmol) was added to the reaction bottle, then THF (70 mL) was added to dissolve the substrate. Pivaloyl chloride (3.3 g, 27.8 mmol) was added dropwise to the reaction bottle under stirring. The mixture was allowed to react at −5° C. for h. Then, the solution of compound 13 (10.0 g, 23.2 mmol) in tetrahydrofuran (80 Ml) was added dropwise to the reaction flask, and after addition, the mixture was further reacted at −5° C. for 3 h, then warmed to room temperature. After the reaction was completed, stirring was stopped, and workup was carried out. The reaction was quenched by adding NH$_4$Cl aqueous solution (50 mL) to the reaction system, and the resultant solution was stirred for 10 min. THE in the reaction solution was rotatory evaporated in vacuum, and then the water phase was extracted with CH$_2$Cl$_2$ (50 mL 3). The organic phase was combined and evaporated to dry. The crude product was purified by silica gel column chromatography. Compound 14 was obtained as white solid (12.1 g), with a yield of 76.0%.

$^1$H NMR (300 MHz, CDCl$_3$): δ (ppm)=7.56 (s, 1H), 7.04 (d, J=7.61 Hz, 1H), 7.00-6.90 (m, 1H), 5.73 (dt, J=18.9 Hz, 9.6, 2H), 5.37 (s, 1H), 5.27 (dd, J=17.0, 1.7 Hz, 1H), 5.15-5.05 (m, 2H), 5.02-4.87 (m, 2H), 4.85-4.55 (m, 5H), 4.35 (t, J=7.0 Hz, 2H), 4.24-3.98 (m, 3H), 3.73 (d, J=12.2 Hz, 1H), 2.74 (m, 1H), 2.48 (d, J=8.4 Hz, 1H), 2.35-2.20 (m, 2H), 2.18-2.07 (m, 1H), 2.06-1.93 (m, 3H), 1.86 (d, J=22.6 Hz, 1H), 1.43 (d, J=3.7 Hz, 3H), 1.41-1.24 (m, 11H), 1.24-1.10 (m, 4H).

Example 26: Preparation of Intermediate Compound 15

To a 100 mL three-neck bottle, was added compound 14 (5.0 g, 7.3 mmol), and then THE (30 mL) was introduced to dissolve compound 14. The reaction solution was cooled to −6~0° C. under nitrogen protection, and then the solution of benzoyl chloride (1.3 g, 9.5 mmol) in THF (10 mL) was added dropwise to the reaction flask, and the mixture was allowed to react for 2 h at the temperature of −6~0° C. Then, solid lithium t-butoxide (0.7 g, 9.5 mmol) was added, and after reacting for 5 h, the reaction was completed by TLC detection (petroleum ether:ethyl acetate=2:1). Stirring stopped. The reaction was quenched by adding $NaHCO_3$ aqueous solution (50 mL) to the reaction system, and the resultant solution was stirred for 10 min. THF in the reaction solution was rotary evaporated in vacuum, and then the water phase was extracted with $CH_2Cl_2$ (50 mL×3). The organic phase was combined and evaporated to dry. The crude product was purified by silica-gel column chromatography. Compound 15 was obtained as white solid (4.8 g), with a yield of 83.0%.

$^1$H NMR (300 MHz, $CDCl_3$): δ (ppm) 7.75 (s, 2H), 7.49 (d, J=7.0 Hz, 1H), 7.42 (d, J=7.0 Hz, 2H), 7.26 (s, 2H), 7.08-6.89 (m, 2H), 5.78 (dd, J=16.8, 10.1 Hz, 2H), 5.39 (s, 1H), 5.19 (s, 3H), 5.03-4.85 (m, 3H), 4.76 (d, J=6.4 Hz, 2H), 4.63 (s, 2H), 4.36 (s, 1H), 4.21 (s, 2H), 4.04 (s, 1H), 3.88 (s, 1H), 2.37 (s, 3H), 2.03 (d, J=3.4 Hz, 2H), 1.73 (s, 2H), 1.62 (s, 2H), 1.56 (s, 2H), 1.35 (d, J=3.4 Hz, 10H), 1.32-1.23 (m, 5H), 0.86 (d, J=7.3 Hz, 1H).

Example 27: Preparation of Danoprevir Intermediate (16) Using Zhan-1B Catalyst 50 mg of intermediate compound (15) was weighed and dissolved in 5 mL of toluene. Nitrogen was introduced into the reaction system, and the mixture was stirred at room temperature for 20 min. Then, 2.33 mg (0.05 equiv.) of zhan-1B catalyst was weighed and added to the reactor. The reaction solution was heated to 90° C. and allowed to react for 4 h. The product was purified by column chromatography, to provide 34.7 mg of Danoprevir intermediate (16) as white solid, with a yield of 72.0%.

Example 28: Preparation of Danoprevir Intermediate (16) Using Zhan-1B Catalyst 50 mg of intermediate compound (15) was weighed and dissolved in 5 mL of toluene. Nitrogen was introduced into the reaction system, and the mixture was stirred at room temperature for 20 min. Then, 0.23 mg (0.005 equiv.) of zhan-1B catalyst was weighed and added to the reactor. The reaction solution was heated to 90° C. and allowed to react for 4 h. The product was purified by column chromatography, to provide 27.1 mg of Danoprevir intermediate (16) as white solid, with a yield of 56.3%.

$^1$H NMR Spectral Data of Danoprevir Intermediate (16):

$^1$H NMR (300 MHz, $CDCl_3$): δ (ppm) 7.60 (t, J=7.5 Hz, 2H), 7.55-7.47 (m, 1H), 7.43 (dd, J=7.6 Hz, 3.4 Hz, 2H), 7.25 (d, J=7.3 Hz, 1H), 7.06-6.89 (m, 2H), 5.55 (dd, J=18.5, 7.9 Hz, 1H), 5.39-5.23 (m, 2H), 5.11 (dd, J=21.9, 8.0 Hz, 2H), 4.73 (d, J=6.4 Hz, 2H), 4.68-4.49 (m, 2H), 4.34 (s, 1H), 4.24-4.13 (m, 3H), 3.90 (d, J=7.1 Hz, 1H), 2.55 (q, J=9.5 Hz, 1H), 2.32 (d, J=22.3 Hz, 2H), 2.13 (d, J=7.5 Hz, 2H), 2.03 (s, 1H), 1.79 (s, 1H), 1.70-1.53 (m, 3H), 1.53-1.35 (m, 4H), 1.30 (d, J=3.6 Hz, 9H), 1.24 (td, J=7.1, 1.2 Hz, 5H).

Example 27 and Example 28 were used as control experiments. The preparation of from intermediate compound (15) to Danoprevir intermediate (16) was performed using the same zhan1B catalyst as that of the present invention. Two different amounts of catalysts were used in both examples. In the following Examples 29-34, Danoprevir intermediate (16) was prepared from the intermediate (15) using the catalyst of the present invention.

Example 29: Preparation (1) of Danoprevir Intermediate (16)

50 mg of compound (15) was weighed and dissolved in 5 mL of toluene. Nitrogen was introduced into the reaction system, and the mixture was stirred at room temperature for 20 min. Then, 0.46 mg (0.005 equiv.) of catalyst IIaa1 was weighed and added to the reactor. The reaction solution was heated to 90° C. and allowed to react for 4 h. The product was purified by column chromatography, to provide 43.7 mg of Danoprevir intermediate (16) as white solid, with a yield of 90.7%.

Example 30: Preparation (2) of Danoprevir Intermediate (16)

50 mg of compound 15 was weighed and dissolved in 5 mL of toluene. Nitrogen was introduced into the reaction system, and the mixture was stirred at room temperature for 20 min. Then, 0.47 mg (0.005 equiv.) of catalyst IIaa2 was weighed and added to the reactor. The reaction solution was heated to 90° C. and allowed to react for 4 h. The product was purified by column chromatography, to provide 42.6 mg of Danoprevir intermediate (16) as white solid, with a yield of 88.3%.

Example 31: Preparation (3) of Danoprevir Intermediate (16)

50 mg of compound 15 was weighed and dissolved in 5 mL of toluene. Nitrogen was introduced into the reaction system, and the mixture was stirred at room temperature for 20 min. Then, 0.49 mg (0.005 equiv.) of catalyst IIaa3 was weighed and added to the reactor. The reaction solution was heated to 90° C. and allowed to react for 4 h. The product was purified by column chromatography, to provide 44.7 mg of Danoprevir intermediate (16) as white solid, with a yield of 92.7%.

Example 32: Preparation (4) of Danoprevir Intermediate (16)

50 mg of compound 15 was weighed and dissolved in 5 mL of toluene. Nitrogen was introduced into the reaction system, and the mixture was stirred at room temperature for 20 min. Then, 0.46 mg (0.005 equiv.) of catalyst IIba1 was weighed and added to the reactor. The reaction solution was heated to 90° C. and allowed to react for 4 h. The product was purified by column chromatography, to provide 43.4 mg of Danoprevir intermediate (16) as white solid, with a yield of 90.0%.

Example 33: Preparation (5) of Danoprevir Intermediate (16) (Increasing the Amount of Substrate)

500 mg of compound 15 was weighed and dissolved in 50 mL of toluene. Nitrogen was introduced into the reaction system, and the mixture was stirred at room temperature for 20 min. Then, 4.62 mg (0.005 equiv.) of catalyst final was weighed and added to the reactor. The reaction solution was heated to 90° C. and allowed to react for 4 h. The product was purified by column chromatography, to provide 438.8 mg of Danoprevir intermediate (16) as white solid, with a yield of 91.0%.

Example 34: Preparation (6) of Danoprevir Intermediate (16)

500 mg of compound 15 was weighed and dissolved in 50 mL of toluene. Nitrogen was introduced into the reaction system, and the mixture was stirred at room temperature for 20 min. Then, 4.63 mg (0.005 equiv.) of catalyst IIba1 was weighed and added to the reactor. The reaction solution was heated to 90° C. and allowed to react for 4 h. The product was purified by column chromatography, to provide 439.3 mg of Danoprevir intermediate (16) as white solid, with a yield of 91.1%.

The results of the above comparative experiments clearly showed that when used in the preparation of Danoprevir intermediate (16), the ruthenium complex catalyst of the present invention has a higher catalytic activity for intramolecular olefin metathesis in comparison with Zhan1B catalyst.

In order to better evaluate the activity and substrate tolerance of the catalyst according to the present invention, the precursor compound (14) (without the protecting of the amino group) of the olefin intermediate (15) is selected to be directly subjected to an intramolecular olefin metathesis, to prepare Danoprevir intermediate (17).

Preparation of Danoprevir Intermediate (17)

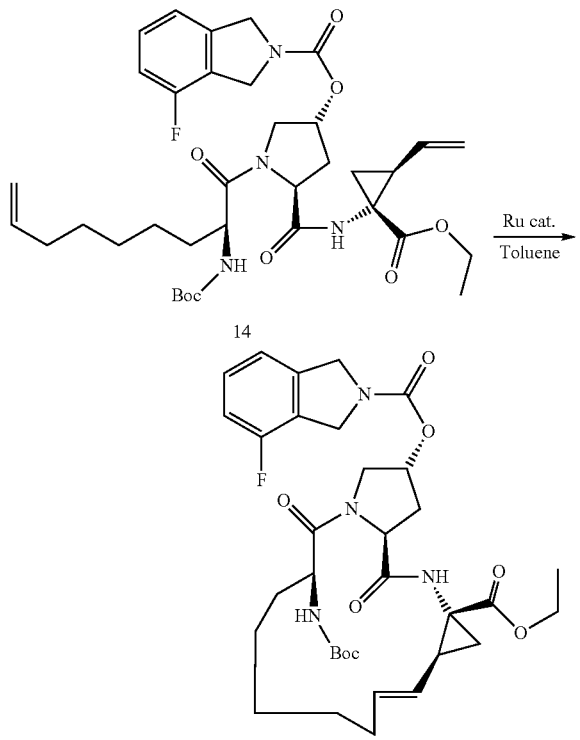

Example 35: Preparation of Danoprevir Intermediate (17) Using the Second-Generation H-G Catalyst 50 mg of compound (14) was weighed and dissolved in 5 mL of toluene. Nitrogen was introduced into the reaction system, and the mixture was stirred at room temperature for 20 min. Then, 1.05 mg (0.025 equiv.) of H-G H catalyst was weighed and added to the reactor. The reaction solution was heated to 90° C. and allowed to react for 4 h. The product was purified by column chromatography, to provide 24.0 mg of Danoprevir intermediate (17) as white solid, with a yield of 50.0%.

Example 36: Preparation of Danoprevir Intermediate (17) Using the Second-Generation H-G Catalyst (Reducing the Amount of Catalyst)

50 mg of compound (14) was weighed and dissolved in 5 mL of toluene. Nitrogen was introduced into the reaction system, and the mixture was stirred at room temperature for 20 min. Then, 0.21 mg (0.005 equiv.) of H-G II catalyst was weighed and added to the reactor. The reaction solution was heated to 90° C. and allowed to react for 4 h. The product was purified by column chromatography, to provide 17.5 mg of Danoprevir intermediate (17) as white solid, with a yield of 36.4%.

$^1$H NMR Spectral Data of Intermediate (17):
$^1$H NMR (300 MHz, CDCl$_3$): δ (ppm) 7.07-6.94 (m, 3H), 5.51 (s, 1H), 5.36 (s, 1H), 5.24 (t, J=9.1 Hz, 2H), 4.84-4.50 (m, 10H), 4.22-4.04 (m, 1H), 2.17-2.01 (m, 4H), 2.01-1.42 (m, 7H), 1.34-1.26 (d, J=2.8 Hz, 9H), 1.24-1.21 (t, J=6.9 Hz, 8H).

Example 37: Preparation of Danoprevir Intermediate (17) (Using the Catalyst of the Present Invention)

50 mg of compound (14) was weighed and dissolved in 5 mL of toluene. Nitrogen was introduced into the reaction system, and the mixture was stirred at room temperature for 20 min. Then, 0.53 mg (0.005 equiv.) of catalyst IIaa1 was weighed and added to the reactor. The reaction solution was heated to 90° C. and allowed to react for 4 h. The product was purified by column chromatography, to provide 43.3 mg of Danoprevir intermediate (17) as white solid, with a yield of 90.2%.

Example 38: Preparation of Danoprevir Intermediate (17)

50 mg of compound (14) was weighed and dissolved in 5 mL of toluene. Nitrogen was introduced into the reaction system, and the mixture was stirred at room temperature for 20 min. Then, 0.55 mg (0.005 equiv.) of catalyst IIaa2 was weighed and added to the reactor. The reaction solution was heated to 90° C. and allowed to react for 4 h. The product was purified by column chromatography, to provide 41.5 mg of Danoprevir intermediate (17) as white solid, with a yield of 86.5%.

Example 39: Preparation of Danoprevir Intermediate (17)

50 mg of compound (14) was weighed and dissolved in 5 mL of toluene. Nitrogen was introduced into the reaction system, and the mixture was stirred at room temperature for 20 min. Then, 0.57 mg (0.005 equiv.) of catalyst IIaa3 was weighed and added to the reactor. The reaction solution was heated to 90° C. and allowed to react for 4 h. The product was purified by column chromatography, to provide 41.1 mg of Danoprevir intermediate (17) as white solid, with a yield of 92.0%.

Example 40: Preparation of Danoprevir Intermediate (17)

50 mg of compound (14) was weighed and dissolved in 5 mL of toluene. Nitrogen was introduced into the reaction system, and the mixture was stirred at room temperature for 20 min. Then, 0.53 mg (0.005 equiv.) of catalyst IIba1 was weighed and added to the reactor. The reaction solution was heated to 90° C. and allowed to react for 4 h. The product was purified by column chromatography, to provide 43.0 mg of Danoprevir intermediate (17) as white solid, with a yield of 89.7%.

Example 41: Preparation of Danoprevir Intermediate (17) (Increasing the Amount of Substrate)

500 mg of compound (14) was weighed and dissolved in 50 mL of toluene. Nitrogen was introduced into the reaction system, and the mixture was stirred at room temperature for 20 min. Then, 5.32 mg (0.005 equiv.) of catalyst IIaa1 was weighed and added to the reactor. The reaction solution was heated to 90° C. and allowed to react for 4 h. The product was purified by column chromatography, to provide 434.0 mg of Danoprevir intermediate (17) as white solid, with a yield of 90.5%.

Example 42: Preparation of Danoprevir Intermediate (17) (Increasing the Amount of Substrate)

500 mg of compound (14) was weighed and dissolved in 50 mL of toluene. Nitrogen was introduced into the reaction system, and the mixture was stirred at room temperature for 20 min. Then, 5.32 mg (0.005 equiv.) of catalyst IIba1 was weighed and added to the reactor. The reaction solution was heated to 90° C. and allowed to react for 4 h. The product was purified by column chromatography, to provide 434.4 mg of Danoprevir intermediate (17) as white solid, with a yield of 90.6%.

The results of Examples for the preparation of Danoprevir intermediate (17) clearly showed that when catalyzing an intramolecular olefin metathesis, the ruthenium complex catalyst of the present invention is more adaptable to the substrate, and has a higher catalytic activity in comparison with the second-generation H-G catalyst.

The catalyst could not be recovered in Example 35 and Example 36.

Since the ruthenium complex catalyst of the present invention had better stability, in order to further evaluate the stability, the following examples showed the activity changes of the catalyst according to the present invention during the cyclic catalysis on the intramolecular ring-closing reaction.

Example 43: Preparation of Danoprevir Intermediate (17) (Recycling of Catalyst)

Catalyst IIaa1 Circulation (the First Time):

500 mg of compound (14) was dissolved in 50 mL of toluene. Nitrogen was introduced into the reaction system, and the mixture was stirred at room temperature for 20 min. Then, 5.32 mg (0.005 equiv.) of catalyst IIaa1 was weighed and added to the reactor. The reaction solution was heated to 90° C. and allowed to react for 4 h. The product was purified by column chromatography, to provide 434.0 mg of Danoprevir intermediate (17) as white solid, with a yield of 90.5%. Meanwhile, the catalyst was recovered.

Catalyst IIaa1 Circulation (the Second Time):

Under the protection of nitrogen, the separated and recovered catalyst and 500 mg of substrate were dissolved in 50 mL of toluene. The reaction solution was heated to 90° C. and allowed to react for 4 h. The product was purified by column chromatography, to provide 418.2 mg of Danoprevir intermediate (17) as white solid, with a yield of 87.2%. Meanwhile, the catalyst was recovered.

Catalyst IIaa1 Circulation (the Third Time):

Under the protection of nitrogen, the further separated and recovered catalyst and 500 mg of substrate were dissolved in 50 mL of toluene. The reaction solution was heated to 90° C. and allowed to react for 4 h. The product was purified by column chromatography, to provide 413.0 mg of Danoprevir intermediate (17) as white solid, with a yield of 86.1%.

The above examples showed that the ruthenium complex catalyst of the present invention could be recycled, and also keep the excited activity and stability during cycling.

The following experiments could show the activity of the ruthenium complex catalyst of the present invention in the olefin metathesis polymerization reaction. Polycyclopentadiene (19) was prepared by ring-opening metathesis polymerization catalyzed by the ruthenium complex catalyst, using dicyclopentadiene (18) as polymerization monomer.

Synthesis of Polycyclopentadiene (19)

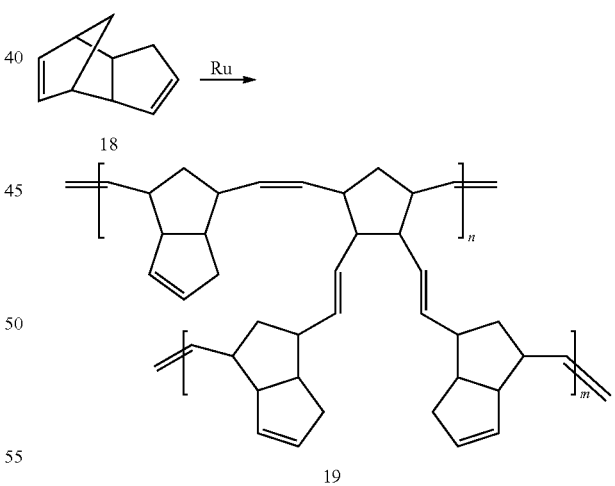

Example 44

1.0 g of dicyclopentadiene (18) was weighed and placed into the reaction flask, to which was added 2 mL of toluene at 35° C. to dissolve compound 18 under stirring, and then under the protection of nitrogen, 0.37 mg of catalyst IIaa1 (monomer:catalyst=30000:1) was added to the reactor. The mixture was heated to 80° C. and stirred for 60 min.

Methanol was added to precipitate the polymer. The polymer was filtered out, crushed, and then dried in a vacuum drying oven at 110° C. for 24 h, with a conversion rate of 96.7%.

Example 45

1.0 g of dicyclopentadiene (18) was weighed and placed into the reaction flask, to which was added 19 mL of toluene at 35° C. to dissolve compound 18 under stirring, and then under the protection of nitrogen, 0.38 mg of catalyst IIaa2 (monomer:catalyst=30000:1) was added to the reactor. The mixture was heated to 60° C. and stirred for 60 min. Methanol was added to precipitate the polymer. The polymer was filtered out, crushed, and then dried in a vacuum drying oven at 110° C. for 24 h, with a conversion rate of 97.5%.

Example 46

1.0 g of dicyclopentadiene (18) was weighed and placed into the reaction flask, to which was added 19 mL of toluene at 35° C. to dissolve compound 18 under stirring, and then under the protection of nitrogen, 0.40 mg of catalyst IIaa3 (monomer:catalyst=30000:1) was added to the reactor. The mixture was heated to 60° C. and stirred for 60 min. Methanol was added to precipitate the polymer. The polymer was filtered out, crushed, and then dried in a vacuum drying oven at 110° C. for 24 h, with a conversion rate of 97.7%.

Example 47

1.0 g of dicyclopentadiene (18) was weighed and placed into the reaction flask, to which was added 19 mL of toluene at 35° C. to dissolve compound 18 under stirring, and then under the protection of nitrogen, 0.37 mg of catalyst IIba1 (monomer:catalyst=30000:1) was added to the reactor. The mixture was heated to 60° C. and stirred for 60 min. Methanol was added to precipitate the polymer. The polymer was filtered out, crushed, and then dried in a vacuum drying oven at 110° C. for 24 h, with a conversion rate of 96.9%.

Example 48

5.0 g of dicyclopentadiene (18) was weighed and placed into the reaction flask, to which was added 10 mL of toluene at 35° C. to dissolve compound 18 under stirring, and then under the protection of nitrogen, 1.84 mg of catalyst IIaa1 (monomer:catalyst=30000:1) was added to the reactor. The mixture was heated to 80° C. and stirred for 60 min. Methanol was added to precipitate the polymer. The polymer was filtered out, crushed, and then dried in a vacuum drying oven at 110° C. for 24 h, with a conversion rate of 96.4%.

The results of the above-mentioned comparative experiments indicated that the ruthenium complex catalyst of the present invention not only had the same application fields as the second-generation H-G catalyst and Zhan catalyst, but also showed significantly better activity in catalyzing the olefin metathesis, including the intramolecular olefin metathesis, the intermolecular olefin metathesis or the olefin metathesis polymerization.

The invention claimed is:

1. An N-heterocyclic carbene ligand of formula Ia or Ib,

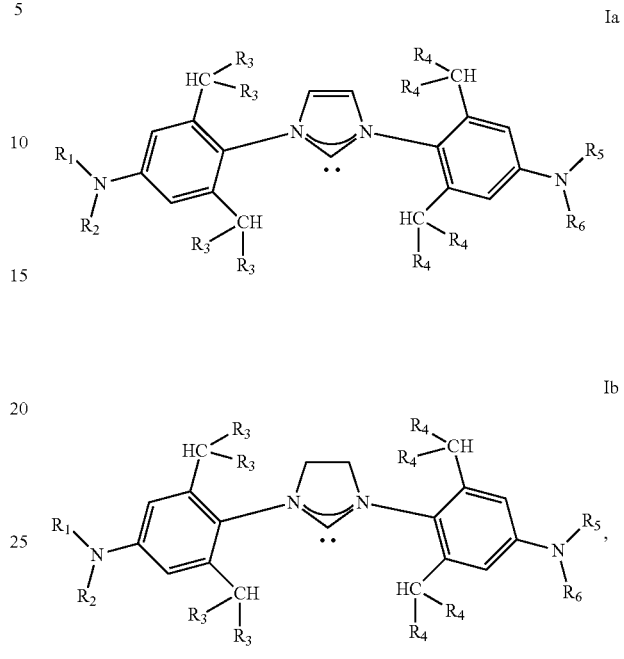

wherein:
each of $R_1$, $R_2$, $R_5$ and $R_6$ is independently selected from the group consisting of $C_1$-$C_{20}$ alkyl or cycloalkyl, $C_1$-$C_{20}$ alkoxy, and $C_6$-$C_{20}$ aryl, or $R_1$, $R_2$, and N to which they are linked form a first heterocyclic group, or $R_5$, $R_6$, and N to which they are linked form a second heterocyclic group, or $R_1$, $R_2$, and N to which they are linked form a first heterocyclic group, and $R_5$, $R_6$, and N to which they are linked form a second heterocyclic group;

each of $R_3$ and $R_4$ is independently selected from the group consisting of substituted or unsubstituted $C_6$-$C_{20}$ aryl, substituted or unsubstituted $C_6$-$C_{20}$ aryloxy, and substituted or unsubstituted $C_2$-$C_{20}$ heterocyclic aryl, wherein at least one of the substituents is selected from the group consisting of $C_1$-$C_{10}$ alkyl, $C_1$-$C_{10}$ alkoxy, hydroxyl, thiohydroxyl, ether group, thioether group, keto, aldehyde group, ester group, amino, imino, amido, nitro, carboxyl, disulfide group, carbonate group, isocyanate group, carbodiimide group, alkoxycarbonyl, carbamate group, and halogens.

2. The N-heterocyclic carbene ligand according to claim 1, wherein $R_3$ and $R_4$ are each independently selected from the group consisting of $C_6$-$C_{20}$ aryl, $C_6$-$C_{20}$ aryloxy, and $C_2$-$C_{20}$ heterocyclic aryl.

3. The N-heterocyclic carbene ligand according to claim 2, wherein $R_3$ and $R_4$ are each independently selected from $C_6$-$C_{20}$ aryl.

4. The ruthenium complex catalyst having the N-heterocyclic carbene ligand according to claim 1, having the formula of IIa or IIb:

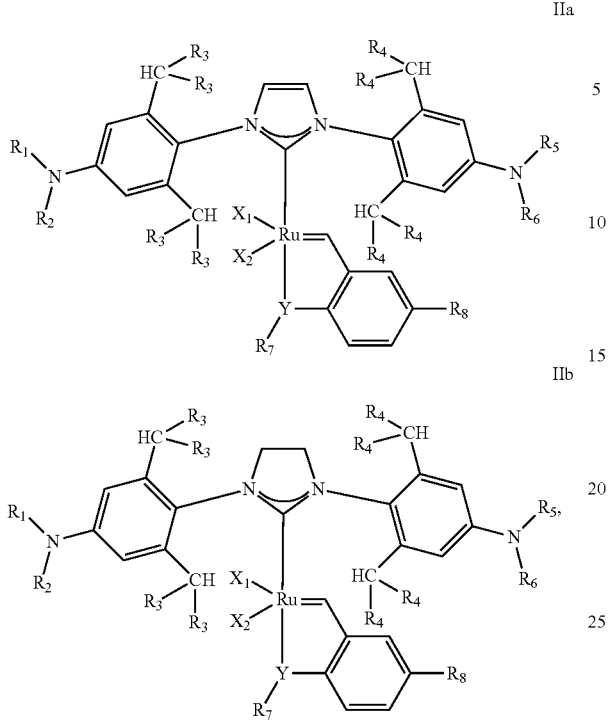

(IIa)

(IIb)

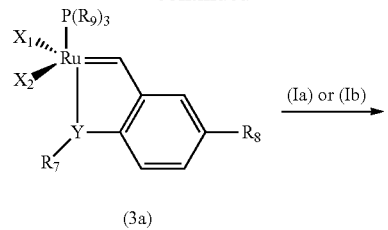

(3a)

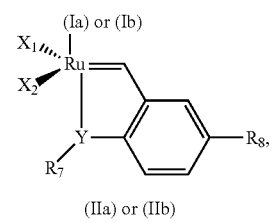

(IIa) or (IIb)

wherein wherein $R_7$ is selected from the group consisting of H, $C_1$-$C_{15}$ alkyl, $C_1$-$C_{15}$ alkoxy, $C_1$-$C_{15}$ thioether group, $C_1$-$C_{15}$ silyl, $C_1$-$C_{15}$ siloxy, $C_6$-$C_{15}$ aryl, $C_6$-$C_{15}$ aryloxy, $C_6$-$C_{15}$ heterocyclic aryl, $C_2$-$C_{15}$ heterocyclyl, sulfinyl, sulfonyl, $C_1$-$C_{15}$ carbonyl, $C_1$-$C_{15}$ ester group, $C_1$-$C_{15}$ amido, $C_1$-$C_{15}$ ureido, and $C_1$-$C_{15}$ sulfonamido;

$R_8$ is selected from the group consisting of H, F, Cl, Br, nitro, nitrile, formyl, $C_1$-$C_{15}$ aminosulfonyl, $C_1$-$C_{15}$ aminocarbonyl, $C_1$-$C_{15}$ carbonyl, $C_1$-$C_{15}$ ester group, $C_1$-$C_{15}$ amido-, $C_1$-$C_{15}$ ureido, and $C_1$-$C_{15}$ sulfonamido;

$X_1$ and $X_2$ are Cl or RCOO—, in which R is $C_1$-$C_{20}$ alkyl; and

Y is O, S, N or P.

5. The catalyst according to claim 4, wherein $X_1$ and $X_2$ are independently chlorine, and Y is oxygen.

6. The catalyst according to claim 5, wherein $R_7$ is isopropyl or isobutyl.

7. The catalyst according to claim 6, wherein $R_8$ is selected from the group consisting of H, nitro, and $C_1$-$C_{15}$ aminosulfonyl.

8. A method for preparing the ruthenium complex catalyst with a N-heterocyclic carbene ligand according to claim 4, carried out according to the following scheme:

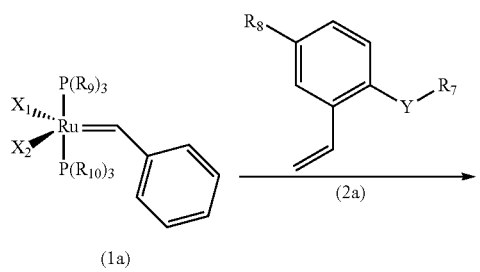

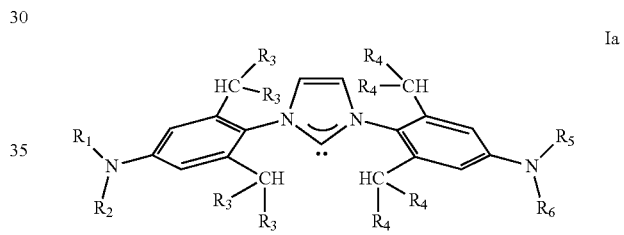

(Ia)

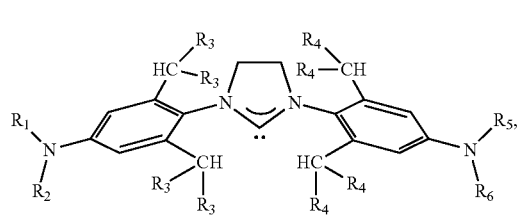

(Ib)

$R_9$ and $R_{10}$ are independently selected from the group consisting of butyl, cyclohexyl, and phenyl; and $X_1$ and $X_2$ are Cl or RCOO—, in which R is $C_1$-$C_{20}$ alkyl.

9. An olefin metathesis reaction catalyzed by the N-heterocyclic carbene ligand according to claim 4, wherein the olefin metathesis reaction is an intramolecular ring-closing metathesis, an intermolecular cross-olefin metathesis, or an olefin metathesis polymerization.

10. The N-heterocyclic carbene ligand according to claim 1, wherein formula Ia is formula Iaa, formula Iab, formula Iac, or formula Iad:

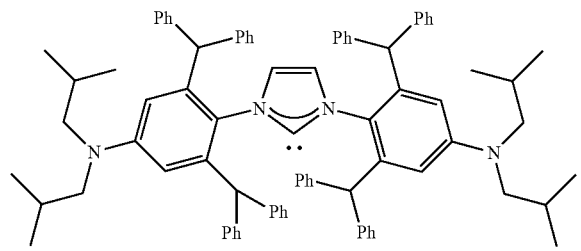
Iaa
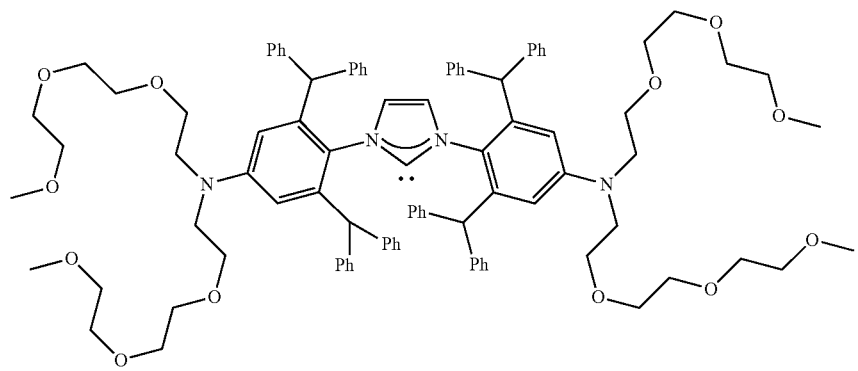
Iab
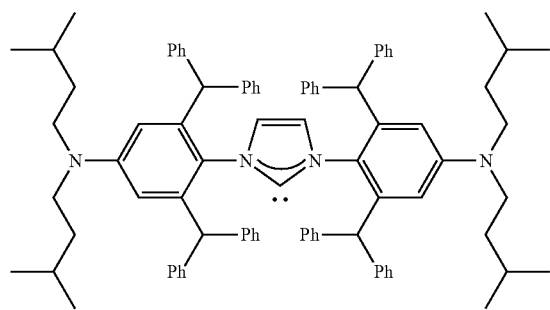
Iac
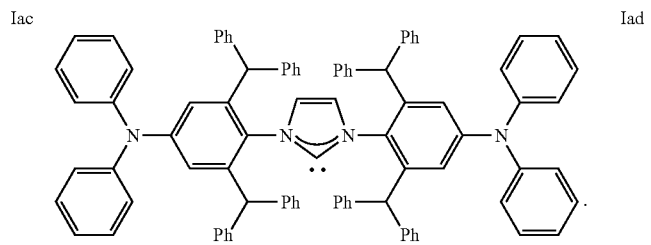
Iad
11. The N-heterocyclic carbene ligand according to claim 1, wherein formula Ib is formula Iba:
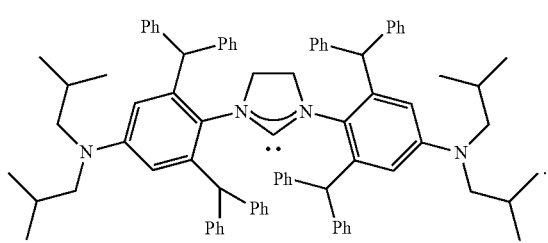
Iba
12. The catalyst according to claim 7, wherein formula IIa is formula IIaa1, formula IIaa2, or formula IIaa3:
IIaa1

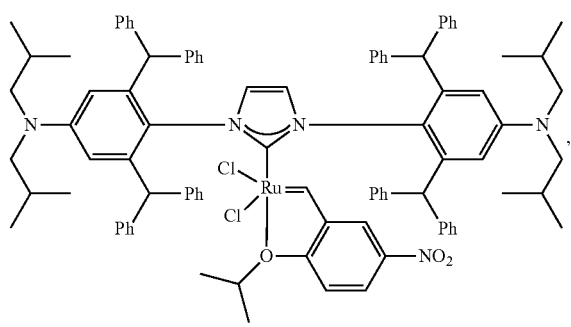
IIaa2
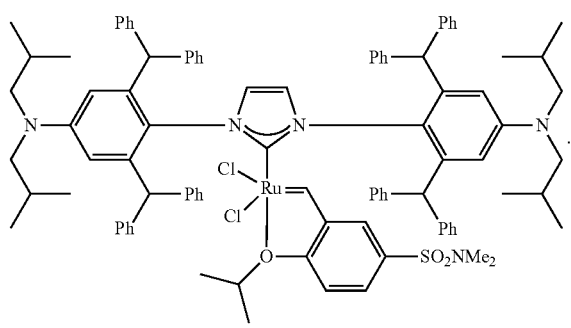
IIaa3
13. The catalyst according to claim 7, wherein formula IIb is formula IIba1, formula IIba2, or formula IIba3:
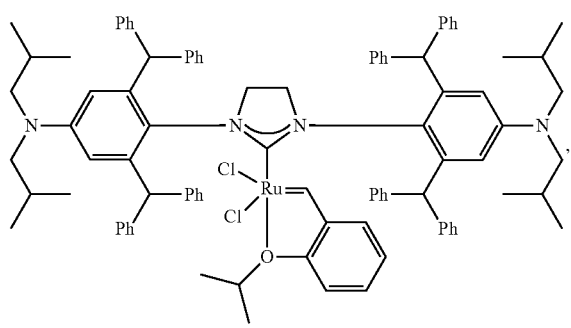
IIba1
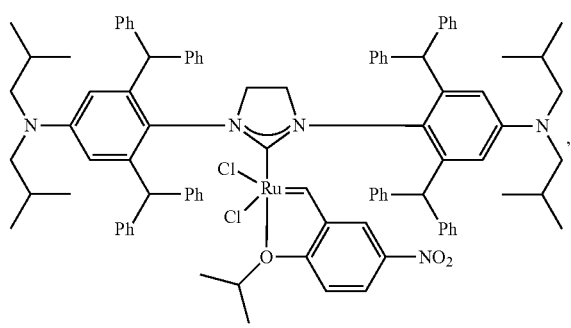
IIba2
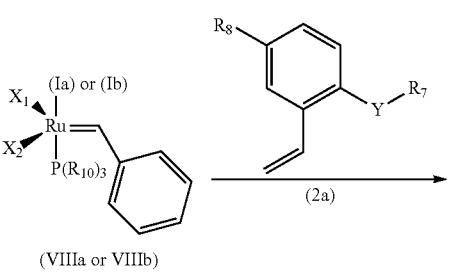
IIba3
14. A method for preparing the ruthenium complex catalyst with a N-heterocyclic carbene ligand according to claim 4, carried out according to the following scheme:
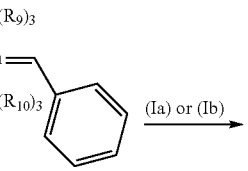
(1a)
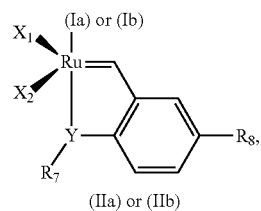
(VIIIa or VIIIb)
(IIa or (IIb)
wherein
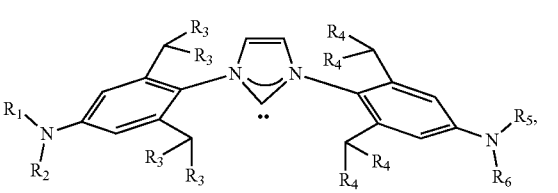
(Ia)

-continued
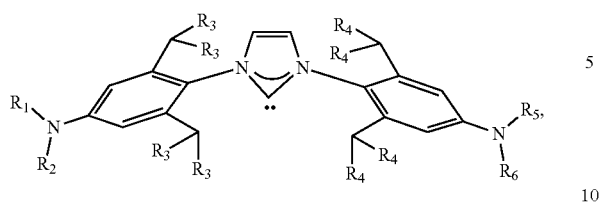
(Ib)
$R_9$ and $R_{10}$ are independently selected from the group consisting of butyl, cyclohexyl, and phenyl; $X_1$ and $X_2$ are independently Cl or RCOO—, in which R is $C_1$-$C_{20}$ alkyl.
* * * * *